US012315632B2

(12) United States Patent
Ianchulev et al.

(10) Patent No.: US 12,315,632 B2
(45) Date of Patent: May 27, 2025

(54) SYSTEMS AND METHODS FOR OPHTHALMIC DIGITAL DIAGNOSTICS VIA TELEMEDICINE

(71) Applicant: Interstat LLC, Sheridan, WY (US)

(72) Inventors: Tsontcho Ianchulev, Harrison, NY (US); Peter Pham, Tomball, TX (US)

(73) Assignee: Interstat LLC, Sheridan, WY (US)

( * ) Notice: Subject to any disclaimer, the term of this patent is extended or adjusted under 35 U.S.C. 154(b) by 572 days.

(21) Appl. No.: 17/579,333

(22) Filed: Jan. 19, 2022

(65) Prior Publication Data

US 2022/0230749 A1 Jul. 21, 2022

Related U.S. Application Data

(60) Provisional application No. 63/155,394, filed on Mar. 2, 2021, provisional application No. 63/139,101, filed on Jan. 19, 2021.

(51) Int. Cl.
| | | |
|---|---|---|
| *G16H 50/20* | (2018.01) | |
| *A61B 3/00* | (2006.01) | |
| *G06F 3/01* | (2006.01) | |
| *G06T 7/00* | (2017.01) | |
| *G06T 7/70* | (2017.01) | |
| *G16H 80/00* | (2018.01) | |

(52) U.S. Cl.
CPC ........... *G16H 50/20* (2018.01); *A61B 3/0033* (2013.01); *G06F 3/013* (2013.01); *G06T 7/0012* (2013.01); *G06T 7/70* (2017.01); *G16H 80/00* (2018.01); *G06T 2207/30041* (2013.01)

(58) Field of Classification Search
CPC ........ G16H 50/20; G16H 80/00; G16H 40/63; G16H 40/67; A61B 3/0033; A61B 3/022; A61B 3/032; G06F 3/013; G06F 3/012; G06T 7/0012; G06T 7/70; G06T 2207/30041
USPC ......................................................... 351/223
See application file for complete search history.

(56) References Cited

U.S. PATENT DOCUMENTS

| | | | | |
|---|---|---|---|---|
| 6,027,217 A | * | 2/2000 | McClure | ............... G06F 3/013 351/224 |
| 6,033,076 A | * | 3/2000 | Braeuning | ............. A61B 3/024 351/224 |
| 6,386,706 B1 | * | 5/2002 | McClure | ............... A61B 3/024 351/237 |
| 2011/0244919 A1 | * | 10/2011 | Aller | .................... G06V 40/168 382/165 |
| 2015/0324568 A1 | * | 11/2015 | Publicover | ............. H04N 23/80 726/19 |

* cited by examiner

*Primary Examiner* — Mohammed A Hasan

(57) ABSTRACT

Disclosed herein are methods, devices, and systems for the enhanced monitoring of visual function via telemedicine to detect early onset of changes and abnormalities associated with disease. The systems include a cloud environment or neural network communicating various tests and images to a client device in which a user/patient is properly positioned to view a display of the client device, receive stimuli, and provide patient input which is evaluated in terms of timing and substance to generate a contrast-sensitivity map of a visual function for the patient. Various ocular tests are described for implementation in a new home-based computer environment rather than using expensive and specific medical equipment in a doctor's office.

18 Claims, 18 Drawing Sheets

SYSTEMS AND METHODS FOR OPHTHALMIC DIGITAL DIAGNOSTICS VIA TELEMEDICINE

PRIORITY CLAIM

The present application claims priority to Provisional Application No. 63/139,101, filed Jan. 19, 2021 and Provisional Application No. 63/155,394, filed Mar. 2, 2021. The content of both of these applications is incorporated herein by reference.

TECHNICAL FIELD

The present disclosure generally relates to telemedicine and more specifically to a methodology and digital/virtual medical devices enabling people to take eye examinations and ophthalmic diagnostic assessments at home using a telehealth platform or other standard computer components used by patients.

BACKGROUND

Normal visual function is essential for quality of life. Many ophthalmologic diseases such as glaucoma, age-related macular degeneration (AMD), diabetic retinopathy, dry eye and others, manifest asymptomatically and therefore early detection and prevention are critical to ensure timely treatment.

Currently, most ocular diagnostic and imaging technology is found in specialized hospitals, clinics or physician offices. Because of the location of such technology, broad deployment and population-wide screening and prevention in the community can be difficult to achieve. There is a cost and complexity associated with the specialized medical equipment that make it nearly impossible to deploy such equipment in a regular home. Additionally, home diagnosis using such equipment without trained medical technicians would not be feasible.

Previous efforts to help patients focus during an ocular diagnosis were developed in the context of a doctor's office. U.S. Pat. No. 7,748,846, incorporated herein by reference, describes a dynamic fixation stimulus but its approach requires a base stimulus to be presented for a period of time and then adjust to an altered stimulus for a period of time. While this stimulus allows for resensitization of the subject's retina, it is not well suited for home ocular diagnosis tests in that a technician is not personally with the patient as would occur in a doctor's office. There is emerging need for diagnostic and imaging tools which can be deployed remotely in the patient's home to enable early detection of vision problems and eye diseases.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

INTRODUCTION

Figure 1:
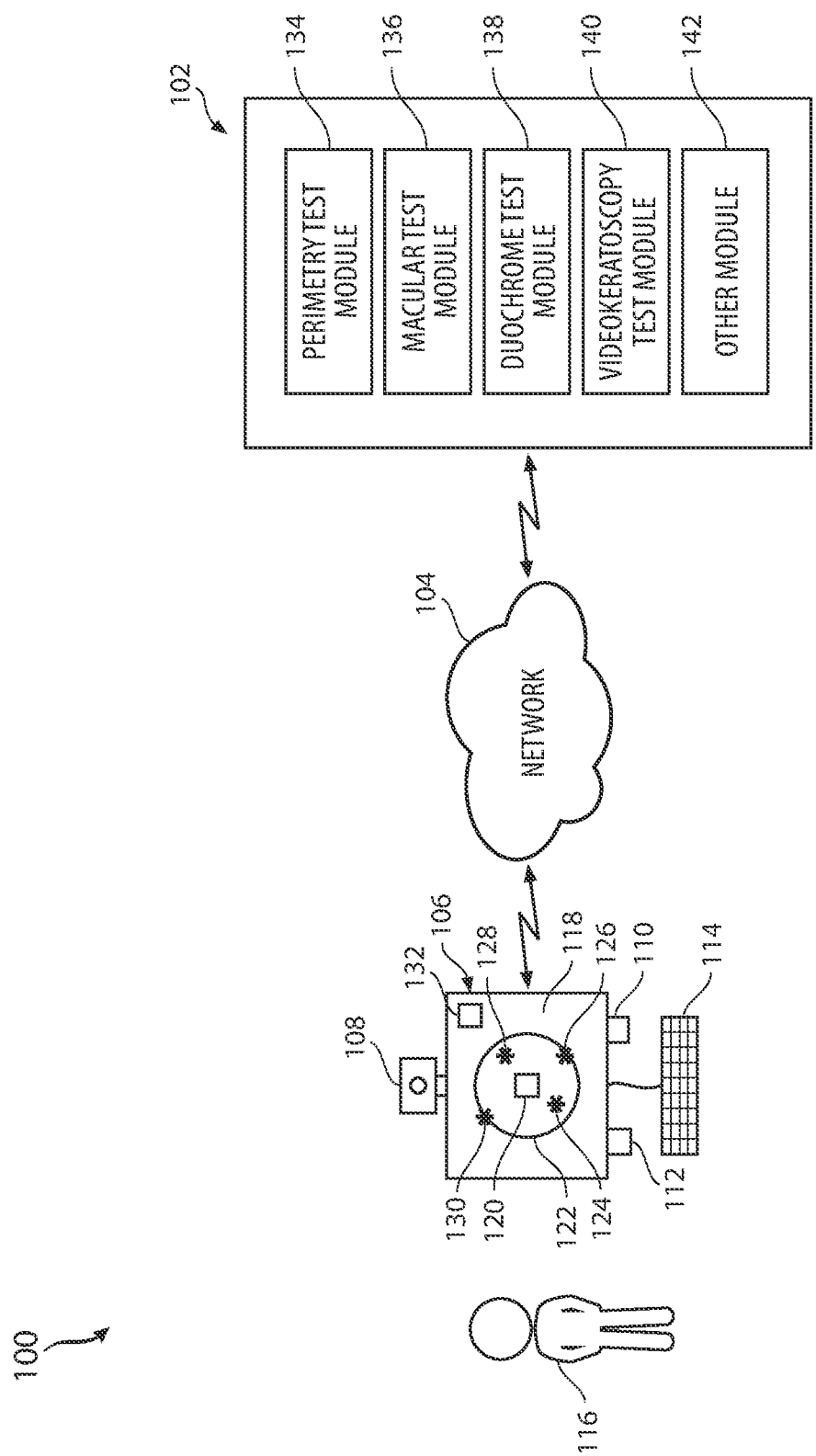
FIG. 1 illustrates an example network structure associated with the disclosure.

Certain aspects and embodiments of this disclosure are provided below. Some of these aspects and embodiments may be applied independently and some of them may be applied in a modular deployment in combination with other device or aspects as would be apparent to those of skill in the art. In the following description, for the purposes of explanation, specific details are set forth in order to provide a thorough understanding of embodiments of the application. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the application as set forth in the appended claims.

The main objective of this inventive method and technology is to deliver several novel virtual specialized hardware-free diagnostic tests online directly to the patient's internet-connected computer, tablet or phone without the need for expensive, specially-designed hardware. Note that "hardware-free" does not mean that no device is used at all. It means specially-designed hardware such as in a doctor's office is not needed to perform diagnostic tests. The approach uses computers, laptops, mobile devices, and so forth that are prevalent in a typical home. When the expensive clinical hardware and specialized personnel are removed, improvements need to be made to the manner in which stimuli is presented to a user on a home-based device as well as how video or image input is provided by the user to achieve the various diagnostic tests that are described herein.

The existing predicates of diagnostic tests are expensive hardware devices/equipment which are only available in doctors' offices. Even using such equipment requires an in-person appointment and a specialist to run the equipment. Thus, the algorithms and devices disclosed herein provide a technical solution to previous problems with the medical equipment used in doctor offices. The various features, modules, algorithms, graphical presentations, video conferencing and virtual technician tools, combine to provide a new framework, platform and technical environment which enable patients at home to take ocular diagnostic tests using their existing computer equipment or equipment that is not designed specifically for ocular diagnostic testing.

The solutions can be presented or made available as applications or models downloaded or embedded on a user device or accessed via a browser on a laptop or desktop computer, or other device. A cloud-based deployment or neural net can be used to generate stimuli, instructions, and to perform analytical analysis of received input as part of an ocular diagnostic test. The tests can be accessed also via technology such as Apple's "App-clips" which represent specific software code that is part of an app but downloaded just for a simple purpose without downloading the entire application.

The disclosed concepts allow optimal, hardware-free, remote testing and diagnostics that can be deployed remotely anywhere as long as there is an interne connection and a connected display/terminal such as iPAD, smart phone, or computer. Cameras can be used as well to help a user position their head properly to take a respective test. In some cases, mobile devices have many sensors that can be accessed by applications. Thus, sensors such as thermal sensors, gyroscopes, and so forth could also be used in various tests.

This disclosure provides a number of different innovations all related to providing in-home evaluation tests for visual problems. Disclosed features include: 1) a perimetry module configured to provide an online perimetry test, 2) a module configured to provide a test for a combination virtual perimetry analysis, 3) a timing module configured for utilizing response times according to an algorithm, 4) a head position module for aiding a user to position their head properly, 5) a macular function testing module configured to provide a dynamic grid or linear/vernier macular perimetry test, 6) a module configured to provide a dynamic quantitative virtual duochrome test, and 7) a module configured to provide a remote unaided digital self-videokeratoscopy test. Other modules are disclosed as well for performing other eye-related tests. Devices can also include two or more combined modules such as modules 1) and 4) or modules 3), 6) and 7).

Thus, the system can include any one or more of these modules in order to enable a patient to receive ocular or other treatments using a computing device in their home or at any other location. These components cause a server or network-based system to be programmed to be a specialized computer system for providing diagnostic tests in new and beneficial ways. The technical improvement includes the elimination of the need for complex medical equipment that would have to be deployed in the home to achieve these tests. The specialized computer systems that operate as described herein represent the technical improvement in terms of using consumer computer equipment for ocular testing with novel methods and programming that previously were not contemplated.

Other technical improvements include such features as instructions and graphical interfaces coordinated with components such as cameras and displays which aid the user in positioning their head. In the old medical equipment in a doctor's office, there are physical aids that make it easy for the user to position their head with the equipment. One benefit of these improvements is that in a time of COVID where people might be more restricted to their homes and less likely to actually physically go to a doctor's office, the patient can still obtain a diagnosis of an eye condition through using one or more of these tests. These and other concepts are disclosed herein.

One example method includes transmitting, from the cloud or neural net to a client device configured outside of a formal medical office, a graphical perimetry test that interrogates 0-100 degrees of a visual field of a patient, the patient being positioned at the client device and not in a medical office. The graphical perimetry test can include an animated and/or gamified element which enhances patient concentration and maintains gaze direction of the patient. The method includes transmitting, from the server to a client device (of any type such as desktop computer, laptop computer, iPhone, iPad, etc.), respective graphical stimuli at various periphery locations as part of the graphical perimetry test, receiving, from the client device, respective patient input in response to the respective graphical stimuli and generating, at the server and based on the respective patient input, a contrast-sensitivity map of a visual function for the patient.

The animated/gamified element can be presented with a gamification approach to presenting the animated element, which provides benefits or points to the patient if they hold their concentration. The animated/gamified element can be positioned in a middle portion of the graphical perimetry test and can by dynamic or moving in size, shape, color or other parameters to keep the patient's attention. The graphical perimetry test can represent an emulation of an office-based perimetry test. In one aspect, the animated/gamified element is a continuously dynamic or changing animated element that maintains the patient concentration. The '846 patent incorporated above requires a base fixation stimulus that is presented for a defined period of time and then is altered in a cyclical manner to sustain the display of the peripheral stimulus. In contrast to that approach, the embodiments disclosed herein can maintain the patient attention better by providing a continuously dynamic or changing animated/ gamified element rather than one that is presented for a time, and then is altered. Such changes can confuse the patent particularly when they are not in a medical office environment.

Other stimuli such as music, changing music, haptic or other input can also be provided to maintain attention for the user.

The method can further include detecting a respective time response associated with the respective patient input, the respective time response including a time between when the patient is presented with the respective graphical stimuli and when the patient provides the respective patient input. The respective time response can be used to generate the contrast-sensitivity map. The approach can also take into account lag time of the network between the user device and a network-based server.

The method can further include applying a positioning algorithm which coordinates with a camera (or other sensor such as an infrared sensor or motion detection or positional sensor) on the client device which is used to confirm that the patient has positioned their head to fit within a framed outline that is graphically presented on the client device as part of the graphical perimetry test. The positioning algorithm can aid the patient in positioning a patient head a certain distance from a display on the client device.

In another aspect, the method further includes receiving positional data at the server from the client device based on data received by the camera (or other sensor) and, based on the positional data, transmitting instructions to the patient regarding moving the patient head to a proper position for taking the graphical perimetry test. The method can also include presenting a virtual technician which the patient can access during the graphical perimetry test. The graphical perimetry test can combine and integrate online visual acuity testing, color vision testing and central macular function testing along with testing perimetry for the patient.

An example system can include a processor and a computer-readable storage device storing instructions which, when executed by the processor, cause the processor to perform operations including transmitting, to a client device, a graphical perimetry test that interrogates 0-100 degrees of a patient visual field of a patient, the patient being positioned at the client device and not in a medical office, wherein the graphical perimetry test includes an animated element which enhances patient concentration and maintains gaze direction of the patient. The operations can include transmitting, to the client device, respective graphical stimuli at various periphery locations as part of the graphical perimetry test, receiving, from the client device, respective patient input in response to the respective graphical stimuli and generating, based on the respective patient input, a contrast-sensitivity map of a visual function for the patient. Various modules can include computer readable instructions which control or cause one or more of a server, a camera, a sensor of any type, a computing device, a display, and user input components to perform the various functions disclosed herein. As noted above, these modules and the new hardware platform disclosed herein can replace or remove the need for specific medical equipment for performing ocular diagnosis on patients and enable patients to take such tests at home.

In one aspect, an application downloaded on the client device presents the animated element and retrieves the data associated with the patient. The data can be analyzed locally or sent to a network-based server for analysis.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

DETAILED DESCRIPTION

Disclosed herein is a new system, a platform, compute environment, cloud environment, network-based server, neural net, marketplace (blockchain, app store, e-commerce), or any other characterization of the system that will enable an improved approach enabling users to maintain focus while taking an ocular test in a home or other non-office environment.

FIG. 1 illustrates an example of the system 100 which is applicable to the perimetry home testing approach disclosed herein. The main objective of this disclosure is to describe several novel virtual diagnostic tests online directly to the patient's internet-connected computer, tablet or phone 106 without the need for expensive hardware. In a perimetry test in a doctor's office, the user positions their head in a bowl-like structure called a perimeter in a dark room. The perimetry test (visual field test) measures all areas of the user's eyesight, including their side, or peripheral, vision. While a strap or other structure aids the user to hold their head in the right position, the user stares at the center of a bowl structure and lights flash in various positions. The patient presses a button each time they see a flash. The lights can be dim to determine whether the user sees a dim light in a certain position. If the user does not see the light, the light can become more bright until the user sees a respective light at a respective position. The test can determine whether the patient has a blind spot or decreased photosensitivity in a discrete area of the field of vision. People with glaucoma often have blind spots or decreased light sensitivity in specific patterns which can be detected using this approach. These visual tests require specialized equipment which is expensive and cause the tests to not be able to be provided in a user's home when they are quarantined or unable to get to a doctor's office.

This disclosure provides a new approach to providing a perimetry test while at their home and without the need of specialized equipment. These new approaches help to improve the accuracy, efficiency and visibility of on-line perimetry testing. Some of the improvements to technology that are disclosed herein include novel functionality, graphical displays, audio presentations, and coordination of computer equipment at a patient's home in order to achieve an acceptable ocular test in ways that previously were not possible.

As disclosed herein, a user client device 106 can communicate via a network 104 such as the Internet with a cloud environment 102. The cloud environment 102 can represent any network-based component such as a cloud-based server, virtual server, hardware server, or any physical or virtual computing environment which can perform the operations described herein to present the ocular tests and the improved features associated with the ocular tests for a user in a non-doctor office environment. Generally, the cloud environment 102 can be called a "server" or a "neural net" which can refer to any of the various embodiments described herein. Such cloud environment 102 can encompass files, applications, databases, data centers, virtual environments, operating systems, networking hardware and software, and so forth, to perform the operations disclosed herein. It can include any components related to one or more of providing a Software-as-a-Service (SaaS) environment, a Platform-as-a-Server (PaaS) environment, an Infrastructure-as-a-Service (IaaS) environment, or a Function-as-a-Service (Faas) environment. The cloud environment 102 can be part of a private cloud, a public cloud, a hybrid cloud, or a multi-cloud environment. In one aspect, the functionality can also be provided via a downloaded application on the device 106.

The client device 106 can include a computer, laptop, iPhone, mobile device, desktop computer and so forth. The client device 106 can be also described as a user equipment that is used by the patient for other purposes besides for use in taking an ocular test such as surfing the Internet at home, checking email, performing computer-assisted tasks such as writing documents or editing images or video. In one aspect, the cloud environment 102 can be called a virtual perimetry device in that it generates and transmits the perimetry test graphical user interface and provides other functionality to a client device 106 positioned with the user 116. The cloud environment 102 can be programmed with various program modules that are configured with computer-readable instructions to make the cloud environment 102 a specialized computer system in connection with the client device 106 and its components. As shall be discussed herein, the cloud environment can include one or more of a perimetry module 134, a macular test module 136, a duochrome test module 138, a videokeratoscopy module 140, and/or an "other module" 140 which can represent a combination of the previous modules or can provide other functionality. The existing predicates of those tests are expensive hardware devices/equipment which are only available in doctors' offices and require an in-person appointment. The disclosed approach includes novel features which helps to replace the bowl-like perimeter structure used in a doctor's office and which aid the user in keeping focused on a fixed point on the user's screen so that the field of vision can be properly probed through various presented lights viewed in their peripheral view using the client device 106 and associated components. In other words, because the user at home will not have the specialized equipment like the bowl-like perimeter, the graphics, audio, and use of components such as cameras or other sensors has be to improve in order to achieve good test results without the specialized medical hardware.

The systems disclosed herein are designed to allow optimal, remote testing and diagnostics without dependency on specialized hardware and/or services found at professional offices that can be deployed remotely anywhere as long as there is an Internet connection 104 and a connected display/terminal such as iPAD, smart phone, or computer 106. As shown in FIG. 1, a patient 116 will typically be at home or can be in some other location (independent of a doctor's office or medical office) and can experience tests to evaluate their visual function remotely via a client device 106 which can include displaying 118 a camera 108, speakers 110/112 and a keyboard 114. Other input/output components can also be included such as a microphone, mouse, multiple displays and so forth. The feature 108 can also represent any sensor such as a thermal sensor, gyroscope, positional sensor, motion sensor, or any other sensor that can be used.

Below are several discrete embodiments related to virtual devices for the remote assessment of visual function. This disclosure first introduces a perimetry testing module 134 that can be configured in the cloud environment 102 for providing the useful functionality to the client device 106. Online perimetry testing is an emulation of standard office-based perimetry which interrogates 0-100 degrees of the patient's visual field to produce a contrast-sensitivity map of the visual function. The contrast-sensitivity map can present to a technician the locations in the visual field of a patient where they have blind spots or ocular issues. Defects in this visual map can be used to diagnose diseases such as glaucoma, optic neuritis and other brain and ocular pathology. While perimetry has been well established in both office-based setting, the virtual perimetry technology disclosed herein has specific inventive characteristics designed to significantly improve its performance and delivery via telemedicine for unaided testing.

One aspect includes a dynamic fixation target 120. The cloud environment 102 can transmit the dynamic fixation target 120 to the client device 106 as part of the testing process. This target 120 can be a gamified and/or animated element used instead of a static fixation target (as would be used in a doctor's office) during the test to enhance patient concentration and maintain gaze direction. Current perimetry algorithms have static, non-animated fixation targets such as a light stimulus or a central circle, at which the patient has to keep looking throughout the entire test. Patient fatigue and attrition of concentration and attention are common with such static, unengaging fixation targets which reduce the accuracy of the overall test. The test can take 2-15 minutes. The use of dynamic fixation targets 120 increases reliability of perimetry testing particularly when the patient is at home and does not have a live medical technician to help them maintain concentration. Other stimuli can also be added to the target 120, such as audio output, haptic output, or other combined or coordinated stimuli to keep the person's attention.

The dynamic fixation target 120 can be an animated virtual element which can occupy, for example, no more than 1-10 degrees (or more) of visual angle and is designed for balanced visual stimulation so that the patient maintains fixation without being distracted from responding to the stimuli 124, 126, 128, 130 presented in the periphery 122 of the display screen 118. The fixation target 120 can be an animated flower, for example. It can even be a small scene like a cartoon with accompanying music and dialog. It can also change through the period of time the test takes. For example, it can start small and grow in size throughout the test. It can change in terms of its size, motion frequency, movement, color, any associated audio, character, etc. The purpose of the dynamic fixation target 120 is to keep the user's attention on the target over the length of time of the test. The dynamic fixation target 120 could be an educational feature that teaches them about a topic. In another aspect, the dynamic fixation target 120 also can be designed not to be too interesting such that the user still is aware of the lights or stimuli 124, 126, 128, 130 that are being presented in their periphery.

The animated fixation target 120 can also change position throughout the entire screen and allow the user to follow it during the test thus changing the user's fixation reference on the screen. Perimetry stimuli can then be displayed with dynamic coordinates in reference to this changing fixation position to maximize perimetry angle of testing on the screen as well as the benefits of a user heightened attention to dynamic moving fixation target during perimetric testing.

In one aspect, the fixation target 120 can be adjusted based on feedback such as from the camera 108 or other patient facing sensor. If the user's head starts to move, or shake, or if the camera detects that their eyes are looking elsewhere, the fixation target can be adjusted to be more interesting, or larger, or change colors, and so forth to regain the user's attention. The system can receive as input data about the issues of the user's head or body and in response to the input data, adjust or change the fixation target 120 or other aspect of the test. Other modalities can also be adjusted such as a haptic response, or a sound can be added to keep the user's attention where it needs to be.

Gamification features can be included with the dynamic fixation target 120. For example, a module can be configured to present the user with points when they respond to one of the stimuli 124, 126, 128, 130 while they are properly focused on the dynamic fixation target 120. The user might be notified of pointed earned by the fixation target 120 itself or by other means such as a haptic output or audio notification. Making proper participation in the test into a game can improve the user's interest and focus during the test. The user may receive a positive audio respond each time they respond, or credits, points, discounts, or any kind of reward can be provided when the properly respond to stimuli or some other aspect of the dynamic fixation target 120. For example, the patient might also receive rewards for each minute they focus on the dynamic fixation target 120. The gamification can present any kind of benefit to the user for their attention to the dynamic fixation target 120 during the test.

In one aspect, if the dynamic fixation target 120 moves around to different locations from the center point, the system can also adjust all of the locations of the stimuli 124, 126, 128, 130 such that the location of the stimuli 124, 126, 128, 130 adjusts depending on the small movements of the dynamic fixation target 120. Such adjustments improve the accuracy of the contrast-sensitivity map relative to the focal point of the user. For example, if the dynamic fixation target 120 operates in a central 1 inch diameter or a central 2 to 5 degrees central portion of the display, then the locations of the stimuli 124, 126, 128, 130 can adjust depending on where exactly the user is focused on when viewing the location of the dynamic fixation target 120. Thus, each stimuli 124, 126, 128, 130 location can adjust within a 1 inch range in a coordinated fashion when the dynamic fixation target 120 is moving in a 1 inch range as well. For example, stimuli 124 might always be positioned 2 inches directly below the dynamic fixation target 120. If the dynamic fixation target 120 moves to the left ½ inch, then the location of stimuli 124 would also move to the left ½ inch. This adjustment improves the results of the contrast-sensitivity map while at the same time helping the user to maintain focus on the stimuli 124.

In one aspect, the experience can include a module configured to provide audio-enhancement to help users maintain their focus, concentration and mental performance through the length of the test. An audio overlay to the visual perimetry interface 118 can be designed to maintain a high state of attention and alertness by playing music via the speakers 110/112. Audio instructions or other audio content during the test can also be presented. Current, perimetry interfaces use only visual sensory input and none use audio-enabled performance enhancing stimulation. Again, the addition of music or other audio in order to help maintain concentration for the user is important when the user is at home or outside of a medical office inasmuch as there is not a doctor or medical technician (ophthalmic trained expert) right with the user taking the test. The music can be chosen based on factors that include the ability to keep the user in a state of concentration but not so soft or smooth as to cause them to get tired and fall asleep. In another aspect, the music should not be too energizing as the user may focus too much on the music and not on the test itself. Music or sounds (like conversation or telling story) can be part of the gamification process of taking the test for the patient as well as noted above.

The music or audio can also be variable in one or more parameters based on feedback provided to the cloud environment 102 which can be obtained from the user input or visual input (or other sensory input) provided to the cloud environment 102. For example, the cloud environment 102 may operate a module or an algorithm which is programmed with computer-readable instructions to evaluate one or more data points which indicate how well the patient is concentrating during the test. The camera 108 might detect head movement or eyeball directions which indicate that the user is no longer looking at the animated element 120. Specifically, the camera may send data back to the cloud environment 102 which can evaluate the image or video to determine whether the user is no longer looking where they should. Motion data, thermal data, infrared data, depth data or 3D data from a 3D depth sensing component or any other data can be evaluated as well.

The type of music that is presented in response to such data can include an increasing tempo or volume which encourages the user to return to a focus on the animated element 120. Thus, the music could have a gentle or slower tempo at the beginning of a test but based on data received during the test, the cloud environment 102 might adjust or modify the music in order to further focus the patient on the animated element 120. In another aspect, the audio may end on a certain note such as a crescendo or a more low key note, and depending on the length of the test or the expected length of the text, certain audio can be selected to pick a song that matches the length of the test.

In yet another aspect, music or audio can also be incorporated into the system and altered stimuli presented in a cyclical manner in the '846 patent, incorporated herein by reference. In one aspect, any feature described therein can be improved via the use of any of the features disclosed in this patent application. For example, the use of dynamic fixation stimuli as described in the '846 patent could be improved by providing such stimuli to a user client device in their home and with the addition of sound or audio which can further assist the user in maintaining focus during the ocular test. Audio could be also presented in connection with the dynamic peripheral stimulations as well disclosed in the '849 patent as well.

The audio stimulation can be based on the feedback to the stimuli. For example, if the user starts to take a longer time to respond to a certain stimuli than the time the user took to respond to earlier stimuli, then the audio can adjust to wake them up or urge the user to focus more.

In another embodiment related to the inventive digital perimetry testing module 134, perimetric brightness/contrast stimuli can be presented through a time-domain generation algorithm. Time-domain generation of stimuli is a continuous or discrete gradual escalation and cycling of stimulus contrast and/or brightness levels for each stimulus presentation over a period of 0.1 sec to 10 seconds. The patient responds (through any one or more of a number of input mechanisms such as a touchscreen, through speech, a gesture, a keypad, a remote control, such as an Apple TV remote, and so forth) when they detect the lowest threshold brightness/contrast level and the system records their response time relative to the stimulus dynamic presentation cycle time which can be further adjusted to the patient individual baseline oculo-motor reflex time. This eliminates the need for multiple separate stimulus presentations at each threshold contrast/brightness level and can streamline and optimize testing.

The perimetry testing module 134 can further be configured to present an embedded virtual technician 132. Perimetry testing is a complex physiometric test and often patients need supervised guidance and coaching during the test. This is typically done by a trained technician who is physically present during the test. The technician can help the user stay awake and help them through the test. The disclosed online perimetry has an embedded virtual technician 132 that can be summoned when the patient needs assistance which can be accessed in the online interface. The virtual technician can appear on the screen to provide guidance and monitoring. This greatly enhances the efficacy and performance of online perimetry. In another aspect, the virtual technical 132 can be presented as a chat, an audio presence or other modality such as a haptic input to a mobile device.

The patient can summons the virtual technician 132 in a number of different ways. For example, the user may move a cursor via a mouse and click on the icon 132 which will cause the virtual technician 132 to appear. The interaction provided by the virtual technician 132 can be trained via machine learning or other approaches to address the current state of the patient. For example, if the patient has had difficulty in concentrating on the animated element 120, and the camera or other sensor 108 identifies a fair amount of head movement of the patient, the system can classify or determine the state of the patient in such a way to initiate or upon request cause the virtual technician 132 to have a comforting demeanor or language. Artificial intelligence, machine learning or other algorithms can be applied to making such a classification. For example, the virtual technician can include an animated entity or person which can speak comforting words to the patient to relax them. The virtual technician 132 might pop up and say "Hi Mary, you are doing great. Take a deep breath. Focus on that point in the middle for another 2 minutes and we'll be done. You are close!" The choice of dialog again can be based upon the data received about the patient state, how much time is left in the test, and/or their ability to concentrate on the animated element 120.

In one aspect, a live technician can be connected via a video conferencing feature to the user 116 through the virtual technician 132. For example, the user might initiate the virtual technician 132 but then ask for a face-to-face discussion with a real technician. A technician at a doctor's office or elsewhere can then, through a computing device and camera, be connected to the client device 106 in the middle of the test. A graphical image of the real technician could be presented on the screen on the side, middle or at any location on the display 118 for the user to talk to. For example, the graphical image or live video of the technician could actually be presented at the focal point. The position of the graphical image of the real technician could be placed strategically. For example, if the user needs to focus more on the central location 120, the image of the technician can be placed near the center so that the real technician can say "Focus here—you can do it, you have 2 more minutes. I'm jumping out now." The screen may be presented on the side, or only audio may be presented so that the user just hears the technician and talks but does not move their head or have any other visual stimulus to look at. Note that although the use of a virtual technician is introduced in connection with the perimetry testing module 134, it can also be utilized in any of the testing modules disclosed herein.

In another aspect, the patient may have a companion at home during the test. A companion computing device such as a mobile phone can be included in the equipment combined to make these tests possible. A phone number of a companion device can be provided to the cloud environment 102 as the test is being set up such that if necessary particular communications can be provided to the companion device to aid the patient. A live technician can be summoned to communicate with the companion device to provide instructions for the companion to help the patient with any aspect of the test.

In another aspect, a live technician can have a display associated with cloud environment 102 or another computing device in which they can monitor how individuals are doing in the course of a home-based telemedicine perimetry test. This live monitoring can occur by virtue of data being transmitted from the client device 106 to the cloud environment 102. The data can include video of the user 116, input responses, timings of user input, data associated with music/audio selected for the test or other data related to the test, and so forth. The data can be processed by a module or algorithm and presented to the technician who can react to the data by communicate with the patient 116 in any number of modalities. Another user device or a camera on the user device 1065 can be used to provide images, video or other data to the live technician who can monitor progress from the cloud environment 102.

The technician can monitor via a display associated with the cloud environment 102 or at some other location in real time the user as they take the test. The image presented to the technician can be an aggregated summary of how the user is doing on their test in real time. For example, a graphical representation of how long the user takes to respond to stimulus could be presented, a graph showing their "state" in terms of concentration or focus could be presented, as well as a graph illustrating how accurate they are in responding to stimulus and what medical conditions appear to be demonstrated via the test. The technician could also be presented with the same screen or images that the user sees and an image of the user via the camera 108 on the client device 106. Thus, the specific display of the technician can include a number of data types of data such as the images that the user sees, plus aggregated or backend data which is related to how well the user is doing on the test and/or other data about the user taking the test related to or indicative of their state, such as their state of concentration. Thus, the technician will receive an integrated display of data and the technician will be able to jump in and participate (audibly, with a video communication, textually, haptically or otherwise) with the user in their home. A technician may also have a display of a plurality of users taking the test and be able to monitor and jump into one of a plurality of people taking the test. An alarm or graded scale of the state of a number of people taking the test can be presented to the technician such that when the color becomes red for one or more users, the technician can be notified and initiate an interaction with each user (or send a virtual technician to jump in) to help them return to a better state to help the users concentrate more, or complete the test properly. The applications that enable this type of functionality increases the efficiency of the user of these home-based perimetry testing technologies.

At the user's home, multiple devices could be arranged such that the user can focus on using one device 106 for the test but another second device would be coordinated or positioned for a live technician to use to monitor the test. The secondary device may provide the camera and microphone as well as speakers such that they can virtually represent a live technician helping the user through the test.

In one aspect, the icon 132 can be used to communicate with a live technician to initiate a video conference, audio conference, chat or other communication. In this case, a live technician could be monitoring a group of people being tested and could receive a notification that a respective user has interacted with the icon 132 (or initiated a discussion in some other manner). The live technician could then utilize the technology to start to connect with the respective user and communicate either via an audio connection, video communication or first mode of audio and a second mode of video. The technician may have data indicating that a companion device (the secondary device mentioned above) should be contacted as well. The technician can review the state of the user and the data from the test and determine what mode to use to communicate with the user. The user might be under a high amount of stress and need a video communication to see the technician and be helped more than just by an audio conversation.

In one aspect, computers now often are configured with multiple displays. The operating system can establish a first display and a second display. The test in this case could be configured to be presented with a first display and the live technician could present data or be presented on the second display to help encourage the user.

In another aspect, the animated element 120 might also be adjusted or modified based on the feedback received at the server 120 with respect to the patient state or condition. For example, if the state of the patient is that they appear to be troubled or unable to concentrate or to continue to concentrate through the test, then the cloud environment 102 might cause the animated element 120 to adjust in certain ways in order to aid additional concentration. Such information or modifications can also come from the live technician in response to an issue with the state of the user.

In one example, the animated element 120 might change from a car to an animal. The animated element 120 might be enlarged and take up a greater proportion of the central area of the display 118. The animated element 120 might turn into a cartoon with different or additional audio. The animated element 120 might turn into a small cartoon scene with speakers and music that might become more entertaining for the user to focus on. Thus, part of this disclosure includes the process of receiving data regarding a patient state with respect to their ability to concentrate and to stay still during an on-line perimetry test presented on a graphical user interface of a client device 106. The data regarding the patient state can then be used to make modifications to the animated element 120 which is positioned in a central location of the display 118 and which helps the patient to focus on a certain location during the test. The data regarding the patient state can also be utilized to make modifications to or decisions regarding the dialog or other aspects associated with the virtual technician 132. Other data such as information known about the patient can also be used by the cloud environment 102 to make decisions regarding how to structure or configure the virtual technician 132 that will interact with the user. For example, one or more of the following parameters associated with the virtual technician 132 can be based upon the patient state data: a gender, a voice, a dialog, topics of conversation, a prosody of the voice, a tempo of the voice, background music, a volume of the voice, a hairstyle, an ethnicity used for the virtual technician, an age, and dialect or an accent, and so forth.

The goal of the virtual technician 132 is to aid the patient in properly taking the test. Therefore, the various input data that is possible as described above can be presented to an algorithm such as a machine learning algorithm or artificial intelligence algorithm or model which can then be used to classify the state of the patient and which can also utilize information about the patient and their history to present one or more of the animated entity 124 or the virtual technician 132 in ways that are calming and helpful to that particular patient in order to help them focus and concentrate.

Another aspect of this disclosure relates to another module 142 or the perimetry module 134 being further configured to provide a combination virtual perimetry test. Existing perimetry tests are monofunctional evaluations for peripheral visual physiometry. They are separate from any other biometric testing and do not provide additional data on the ophthalmic state of the eye. The combination virtual perimetry is specifically designed for simultaneous multiplex assessment by combining and integrating online visual acuity testing, color vision testing and central macular function testing along with perimetry. These various testing approaches can be combined in the online perimetry test presented to the user 116 such that a multiplex assessment can be achieved for the patient.

Visual acuity online in combination with virtual perimetry can be presented as part of the same test. It is important to know the patient's visual acuity and then the virtual perimetry. In this aspect, the module 142/134 can be configured to present on-line a visual acuity test and determine a visual acuity result. If the user is in a certain range of visual acuity, say between 20/20 and 20/60, for example, then the user can continue and take the virtual perimetry test. In another aspect, if the user has a visual acuity of 20/100, then the user should first see their doctor before continuing with the virtual perimetry test. If the user is partially blind, it does not make sense to continue with the virtual perimetry test. These phases can be built into modules configured to present the on-line test. All of the inputs and communication related to providing a pre-test for visual acuity can be included within this disclosure.

One aspect of this disclosure relates to another module 142 or the perimetry module 134 further configured to provide a response time algorithm to create a reflex perimetry—which includes not only visual contrast and brightness threshold data for each perimetry location, but time response parameters as well. Such algorithm can operate on the cloud environment 102 as part of the functionality disclosed herein. Existing perimetry tests only record positive or negative responses to visual stimuli but do not record the time it takes for each response. The disclosed virtual perimetry device 102 incorporates a time response algorithm and, for each perimetric coordinate and each visual stimulus, it records the stimulus response time in milliseconds relative to when the user was presented with the stimulus. Other time parameters can be used as well. This data creates a time response map in addition to the contrast-sensitivity map which clinicians can use to evaluate and diagnose neurologic deficits and conditions. For example, if the user has Alzheimers, Parkinsons disease or other medical issues, their response time to stimulus may be slower and may even be slower according to particular patterns. The algorithms evaluate the user input with respect to time can help even to detect such conditions which may or may not be related to a patient's eye condition. For example, a normal response time might be 200 milliseconds, but with Alzheimers, the user may respond in 800 milliseconds. A normalgram of this data can be used to diagnose other medical conditions.

A machine learning algorithm can be trained on the type of data that is gathered as described herein. For example, user input relative to light stimulus in a visual testing application on the type of equipment described herein, including timing data, can be used to train a machine learning algorithm which can identify, from the input data, possible medical conditions of the person taking the test. Thus, the timing element can become important for a number of different reasons beyond simply how long it takes a user to respond to a visual stimulus.

In another aspect, as patients receive treatment for conditions such as Alzheimer's, they may be able to improve their response time from 800 milliseconds to 300 milliseconds. The technologies disclosed herein can be utilized to evaluate how people are responding to treatment to such medical conditions over time. For example, visual tests as those described herein can be provided to an Alzheimer's patient throughout treatment to determine if their response time is improving. This application of the test may be completely independent of any actual visual test that is needed but rather is primarily used to test patient improvement for another medical conditions which can be tracked in terms of user response times to visual stimuli.

In this regard, included within this disclosure would be visual stimulus which may not have any specific value in terms of probing the visual condition of the patient eyes, but rather can simply be used to test a user response time. Thus, a different type of stimulus might be used for a person who is being tested for improvement to an Alzheimer's treatment as opposed to a user who is having a virtual perimetry test.

The time response algorithm can also take into account a lag associated with the time needed to transmit data over the network 104. For example, the desired time involved with the time between a stimuli 104, 126, 128, 130 being presented on a display 118 for the patient 116 to see and the time thereafter it takes for the user to respond to the stimuli using the keyboard 114 or other input device associated with the client device 106. Because the time that the stimuli is presented on the display 118 is later than the time that the data associated with the stimuli is transmitted from the cloud environment 102, the system can determine through testing, network analysis, packet analysis, or other network analysis techniques, how to take into account the transmission delays inherent in communicating data over the network 104. For example, the system may determine that the time between when the stimuli 124 is transmitted from the cloud environment 102 (say at T1) to when it is displayed to the user (say at T2) is 10 milliseconds. Assume that it takes the user 5 milliseconds to respond to the stimuli 124 (say T3=5 milliseconds). The system may determine that the return time from when the user clicks on a mouse or a keyboard (at T4) to when that data is received at the cloud environment 102 (T5) is 8 milliseconds. Considering these example parameters, from the time the cloud environment 102 transmits the stimuli 124 to the time it receives the user input associated with that stimuli is 23 milliseconds. However, taking into account the lag time for T2 and T5, the system can determine the response time for the user to be 23−18=5 milliseconds and then use that value in its calculations and generation of response maps.

In another example, to remove the factor of lag over a network, a local application on the device 106 might be used to present stimulus and receive the user input. Time stamps can be used locally to more accurately determine exactly when a stimulus 120 is presented and then the input from the user is received.

Time stamps can also be used such that a timestamp can be associated with when data is transmitted, when presented on a display, when received from a user, when transmitted from a server, received at device and/or when a user reacts to a stimulus. For example, a timestamp associated with when a stimulus is presented on a display, when compared to a time stamp associated with a patient response, can provide the necessary timing data to evaluate the patient condition.

Figure 2:
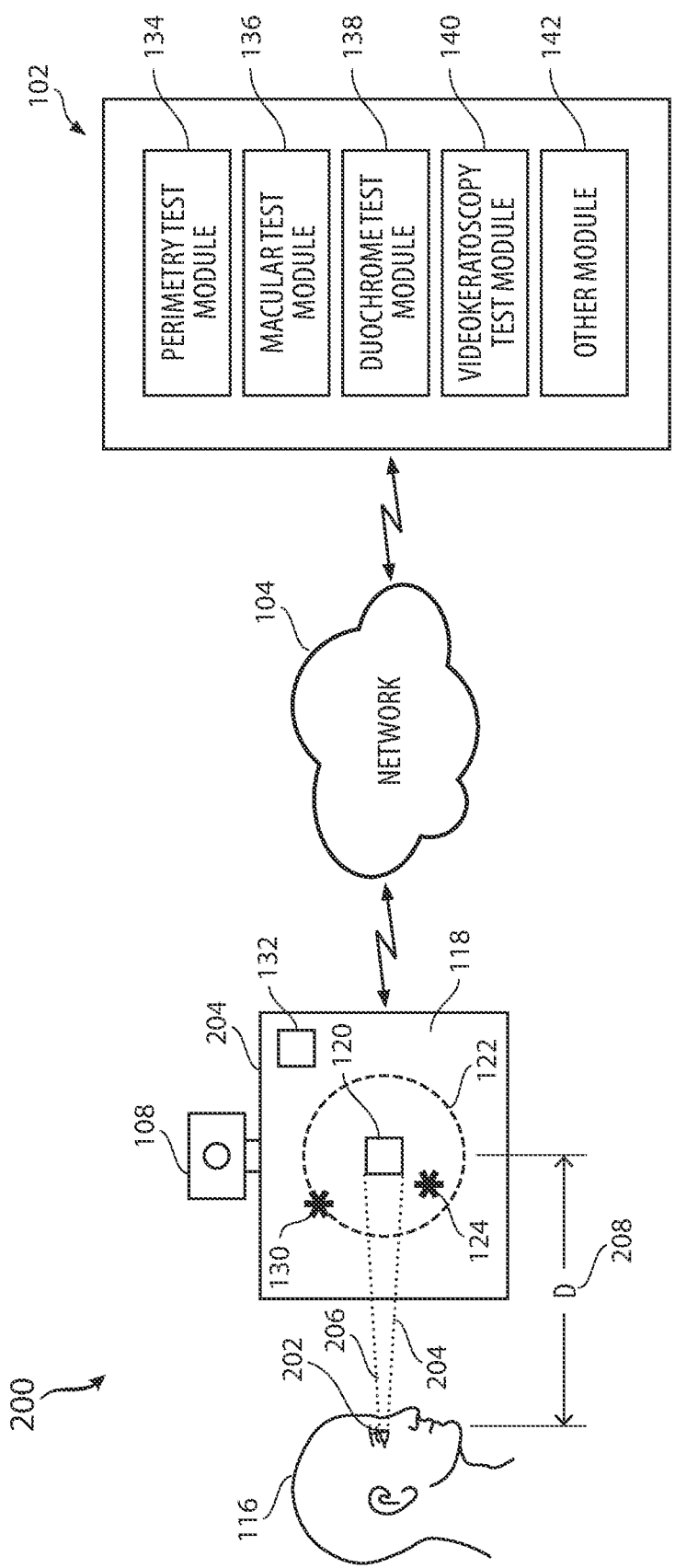
FIG. 2 illustrates a patient position relative to a client device.

Another aspect of this disclosure relates to a module 142 configured to operate a high precision algorithm for head positioning. FIG. 2 illustrates this approach 200. Telemedicine-based unaided vision function tests perimetry (and also other ophthalmic tests such as refraction) can rely on accurate head position and ocular distance 208 from the screen. The approach disclosed herein utilizes a perimetry positioning algorithm whereby the camera 108 is employed to gather data to help a patient position their head 116 to fit within a framed outline 122 to position the eyes 202 properly when the head is at a certain pre-specified distance 208 from the monitor 118. This will ensure proper positioning of the head from the screen as well as the accurate visual field angle for interrogation and testing.

An aspect of the head positioning algorithm is that the system can receive data from the camera 108 with respect to a position of the user's head 116 relative to the display 118. The outline 122 presented on the display 118 can guide the user with respect to where they position their head 116. The cloud environment 102 can utilize information about the position of the camera 108 relative to the display 118 (i.e., is it determined to be on top, on the side, incorporated into the display, etc.), and to make adjustments regarding how to determine the position of the patient's head 116 relative to the element 122. In order to assist the patient in properly positioning their head, the cloud environment 102 can provide instructions via the virtual technician 132, can make adjustments to the element 122, can move an animated element 120 in the middle portion of the screen 118, can provide audio instructions such as "tilt your head down" or "please raise up approximately 2 inches", and so forth. The system can highlight or adjust portions of the element 122 to indicate that the user should move a certain direction, including closer to or farther away from the display 204.

These instructions or modifications to the system output are based on positional information received by the camera 108 as well as other potential means of receiving data. For example, audible data might also be received at a microphone associated with the client device 106 which can be used to determine a position of the user's head 116. In another aspect, facial recognition technology can be used, such as is used by an iPhone or other mobile device, to detect a person's face and unlock the device. Such data can be helpful to assist in positioning the user's face at the right distance and orientation. These additional aids in properly positioning the user are useful in the context disclosed herein in which a live technician is not sitting personally with the patient to help them get properly positioned. Therefore, these innovations improve the experience of the patient and help them to get properly positioned in order to take the various tests disclosed herein from their own client device at home.

In another aspect of performing a digital perimetry test performed via a perimetry test module 134, a 3D depth-sensing, oculocephalic scan-and-track telehealth perimetry test can be performed via consumer electronic device including a user's mobile device. A digital perimetry test as described above can be further enhanced where one or more 3D depth scanning camera(s) on a monitor, mobile device or screen (such as TrueDepth (TD), Time-Of-Flight (TOF), LIDAR, sonar, ultrasonic or other sensor systems on mobile devices, including artificial intelligence (AI) enhanced 3D depth sensing extrapolations and enhancements of the above as well as regular cameras) can be used for high-precision head positioning and the maintenance thereof, before and during a perimetry test. The 3D depth sensing can enable the system to identify how far away a user's head or eye(s) (or any other object) is from the phone. The 3D data can also be used to identify orientation of the head or any other object as well. The sensor or 3D depth scanning camera can be front-facing in one aspect. Feature 108 can represent a 3D depth scanning camera.

In another aspect, a digital perimetry test as described above can also be enhanced where a 3D depth scanning camera on a monitor, mobile device or screen as described above can be used for eye tracking and fixation monitoring and maintenance, before and during a perimetry test, and to dynamically adjust stimulus position based on eye tracking position. In another embodiment, two or more monitors, or two or more mobile devices can be used simultaneous to increase accuracy and reliability of 3D depth sensing.

A further modification of the digital perimetry test as described above can include a one or more 3D depth scanning camera(s) on a monitor, mobile device or screen as described above can be used for eye tracking and 3D eye position and pupillary distance inference which can enable monoscopic or bilateral off-axis image projection, before, during or after a perimetry test. The use of parallax effect and dynamic 3D off-axis image projection can be deployed for optimized fixation, targeting and centration before and during the perimetry test. A technical overview of off-axis parallax monoscopic imaging can be performed using such features as Apple's ARKit's face tracking to track the user's face and adjust the image on the display accordingly, which can make the image look like it's coming out of the screen as the person moves. The ARKit provides example code for tracking and visualizing faces and operates to detect faces in a front-camera alternative reality experience, and then overlay virtual content and can animate facial expressions in real time. One of skill in the art will understand Apple's ARKit operations can capabilities.

A 3D head tracking or face tracking application can use the TrueDepth camera to allow for inferring the 3D positions of the user's eyes. A system can use the position of the eye and the device screen rectangle shape, to define a non-symmetric camera frustum. This allows for the rendering on the device to make it appear as 3D objects extending in front of or behind the screen of the device. Such technology can be applied to the present context for providing a digital perimetry test. It is noted as well, that the presentation of objects that appear to be 3D on a mobile device screen using the non-symmetric camera frustum can also be used for testing the user's vision in any of the tests described herein. For example, the 3D image could be of a tall cylinder and the user could be instructed to move their mobile device until all they see is the top circle of the cylinder as though they are looking direction down at it. The 3D rendering and approach in this regard could thereby by used to aid the user in properly positioning the device relative to their eyes. Such an approach (using 3D rendering as the object 120 based on the user's facial position) can also be used to make the perimetry test more interesting and to maintain the user's attention as well through the test.

Another test that is possible to be provided through the systems disclosed herein is a macular function test, implemented by the macular testing module 136 in the cloud environment 102, which incorporates several elements: 1) a Vernier macular perimetry test, 2) a grid perimetry test and 3) a photoreceptor stress test. A person's acuity becomes very sensitive when the user detects breaks in a line. Vernier acuity relates to the ability of the eye and the retina function to detect very small and subtle breaks and defects in a line segment when displayed in the central and para-central vision. With macular degeneration or diabetic macular disease, these breaks become harder to see and the image looks black. The virtual perimetry interface disclosed herein has a novel linear perimetry algorithm to interrogate the retinal function for any perceptual changes or defects in a bi-linear segment in order to create a functional retinal scan for metamorphopsias and/or scotomas.

Other aspects of the macular testing module 136 are discussed next. A central retinal function scan disclosed herein can be designed as an on-demand cloud-based digital health application 102 for home monitoring that can be delivered to any web-connected device such as smart phone, tablet, laptop or desktop 106. A hyperacuity testing can use both horizontal and vertical bi-linear scans of the central 10 degrees (or other angle) of a patient's view. It is a 3-minute multi-modal test with a foveal acuity test, dynamic photostress Amsler grid test and hyperacuity Vernier central function scan to detect defects such as scotomas and metamorphopsia. Like Snellen visual acuity (the known Snellen eye chart that is used to measure visual acuity), hyperacuity reflects the eye's ability to see fine detail, but with much higher sensitivity. Hyperacuity testing is approximately 10 times more sensitive than Snellen visual acuity, with a range of 3 to 6 seconds of arc vs Snellen 30 to 60 seconds of arc. It is also less sensitive to age and blur which makes it particularly useful for macular function assessment.

Figure 3:
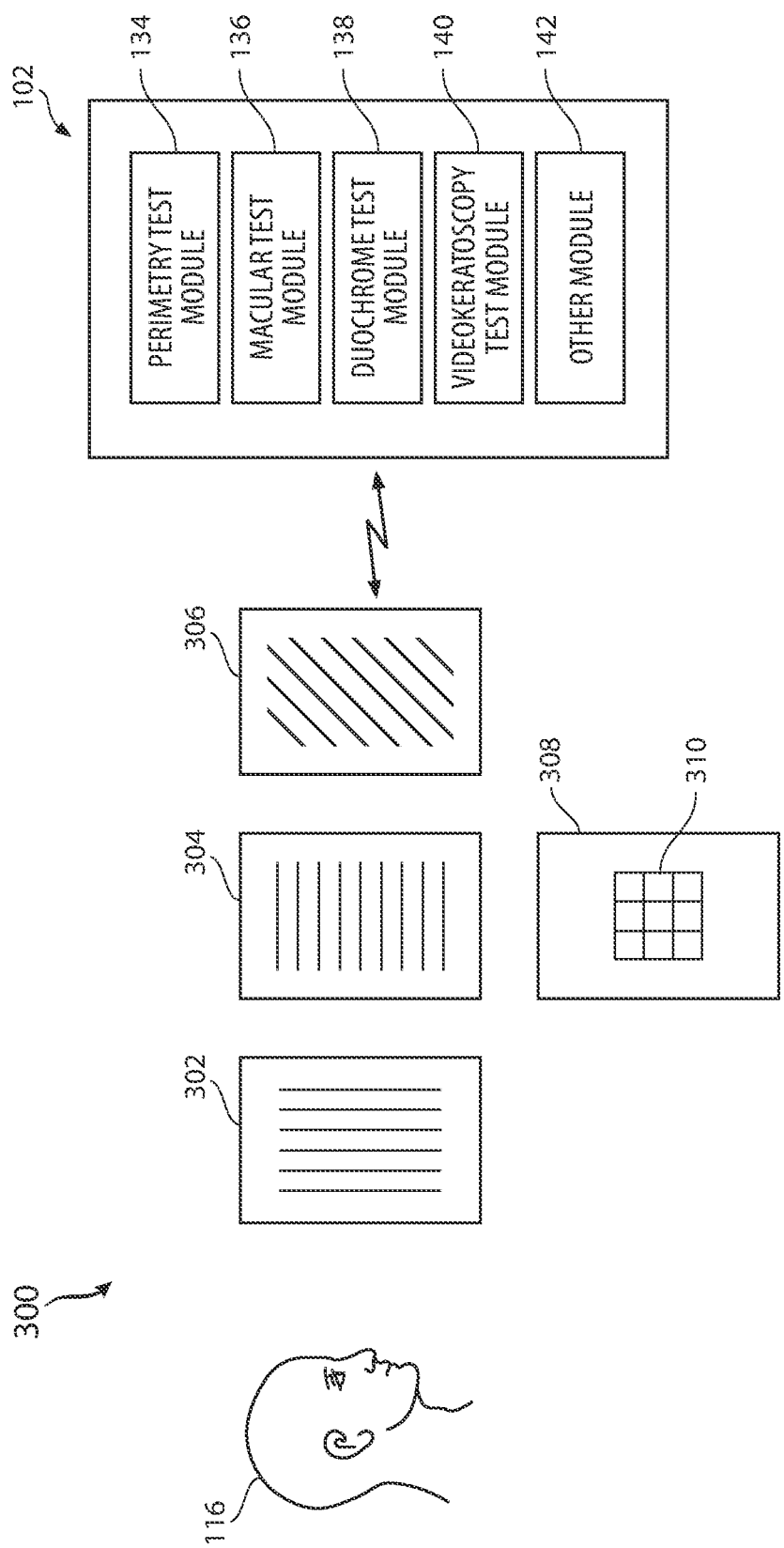
FIG. 3 illustrates example testing input on a display screen of a client device.

The Vernier macular perimetry test is disclosed in the various images 300 shown in FIG. 3. The linear algorithm can include the presentation from a cloud environment 102 and graphically of 1-10 continuous parallel lines in horizontal 302, vertical 304 or angulated orientation 306, separated by no more than 10 lines thickness width in between. Other ranges can also be included in terms of how many lines of thickness width needs to exist. The lines appear on the screen in maximum or variable brightness and the patient 116 responds by indicating (click, touch screen, keyboard input, etc.) which line(s) are abnormal. The patient 116 can be enabled to use a cursor or pointer to show exactly where on the display 118 the lines are broken. If the retina has any type of disease, this type of test can help to detect retinal distortions and problems that normally would be missed as these issues would be blended with other images user sees. Thus, the macular test module 136 will transmit or present the line patterns and receive focused user feedback which can be analyzed to determine if there is a visual issue.

In one aspect, lines can be presented one by one or in groups. In some cases, a grid is confusing and hard to see at the same time. Two lines or more at a time can be presented and then fade. Another pair can be presented in a new position. In this manner, the locations of the lines can be presented in a serial fashion so that a patient taking the test can be probed in their field of vision with respect to retinal distortions. By registering the lines and their coordinates which have defects such as scotomas and metamorphopsias, the system can ascertain the location of the macula physiometric defects and whether there is disease progression when they get bigger.

In this regard, the cloud environment or neural net 102 can send one or more images of lines (or a series of lines) as described above and shown by way of example in FIG. 3 and then receive the data from the patient 116 on their client device 106. There are a number of different ways in which the user could respond to indicate which lines appear to be abnormal. As noted above, the user might click on a line or on the image that shows where the abnormality is shown. The display 118 can present a series of grid lines at specific locations and the user may simply speak and say—"the line in grid location 64" is distorted. With assistance of AI based on continuous monitor of user behavioral input from presented test patterns, enhanced detection and localization of macular abnormality via this method can be obtained. In other words, the user interaction might be audible or multimodal in connection with any test disclosed herein. A touch sensitive screen can be used so that the user can indicate where on the screen the abnormality is. The cloud environment 102 can receive the user input in connection with the respective set of lines that are presented as part of the Vernier macular perimetry test and evaluate the patient visual condition based on the received input.

The ARKit could also be programmed to evaluate where the user is looking on the screen to determine the location of their view on the line pattern when they indicate where the abnormality is.

In another aspect, the Vernier perimetry test can include the following features. The central retinal function of the patient's eye can be scanned from 0-20 degrees, inclusive, from a fixation point on either side and can be scanned functionally for defects such as metamorphopsias and scotomas using linear Vernier perimetry with one or more of the following characteristics: (1) one or a multitude of lines not fewer than two and not more than 5 linear elements; (2) variable contrast and color in the linear elements; (3) each line can be 0.1 mm to 5 mm thickness, inclusive; (4) linear separation between the lines can be 0.1 mm at a minimum to 5 mm at a maximum, inclusive; (5) sequential display or animated presentation can be provided within the central field; (6) the system can record the response to detected abnormalities within the linear scan; (7) the system can register the location and extent/size of the defects by determining the coordinates of the abnormal linear scan elements; and (8) the system can monitor central retinal disease progression using Vernier scans over time and register the size and location change in the abnormal linear elements. This method is further described below in FIG. 10B.

The Vernier macular perimetry test can also be enhanced using a 3D Depth-sensing, to introduce an oculocephalic scan-and-track telehealth macular function testing via a consumer electronic device including a mobile device. A digital macular function test as described above can be enhanced with a one or more 3D depth scanning camera(s) on a monitor, mobile device or screen (such as TrueDepth (TD), Time-Of-Flight (TOF), LIDAR, sonar, ultrasonic or other sensor systems on mobile devices or desktop devices, including AI-enhanced 3D depth sensing extrapolations and enhancements of the above as well as regular cameras) can be used for high-precision head positioning and the maintenance thereof, before and during a macular function test. The technology can also be used for eye tracking and fixation monitoring and maintenance, before and during a macular function test.

The technology can also be used for eye tracking and 3D eye position and pupillary distance inference which can enable monoscopic or bilateral off-axis image projection, before, during or after a macular test. The use of parallax effect and dynamic 3D off-axis image projection can be deployed for optimized fixation, targeting and centration as well as 3D macular grid or line scan projection before and during the macular function test. As with the other test, the apparent 3D renderings on a screen can also be used as part of a Vernier macular function test as well. Data from multiple cameras can be used sequentially or simultaneous to analyze for depth, location, or movement for any test disclosed herein.

Another potential test which can be provided by the system described herein is a dynamic quantitative virtual duochrome test provided by the duochrome test module 138. The duochrome test module 138 can be generated with computer-readable instructions to present this test from the cloud environment 102 to the client device 106. This test evaluates different colors as a user's retina focuses differently based on color. The test can probe whether a person glasses are correct for their eyes. If a red side and a green side are the same visually to a user, then their glasses are in focus, and if the sides are not the same, then the glasses are out of focus. Again, user input in the context of this test can be evaluated to test for duochrome issues.

Current duochrome tests are static and rely on qualitative assessment of whether the optotype on a green background is equally perceived as the optotype of a red background. The inventive adaptation disclosed herein of the duochrome test employs a dynamic response managed by the duochrome test module 138 in the cloud environment 102 where the patient toggles a response key 114 (or uses some other modality such as speech, gesture, or other input) which varies the relative background brightness between the red and the green fields. The cloud environment 102 coordinates the presented relative background brightness between red and green fields see on the client device 106 and the patient input to evaluate the patient perception of the relative background brightness between the different colored fields. By finding the point of equivalent perception, a relative brightness difference which is quantifiable can be used to measure the magnitude of refractive error of the eye and that value can be monitored over time. This dynamic virtual and quantifiable test can be deployed via telemedicine for unaided patient physiometric testing of the ocular system.

This test takes user input and changes the colors, shapes, patterns, size and so forth based on the user input or interactions to fine tune the position of the focal point and how far they are from the optimal focal distance for the eye. The interactive nature of this test improves the input and data obtained to more accurately test whether a user's glasses are proper.

Another test that is possible through the disclosed system and programmed modules, and particularly as an enhancement to the perimetry test module 134 described herein, is a grid macular perimetry test. Currently, macular tests evaluate, as users look at the grid, whether the user has problems with their central retina. The macular test disclosed herein uses a similar concept but, based on duochrome test, the cloud environment 102 can change colors, change the size and change the position and the movement of the grid, to fine tune and localize the abnormality on the retina. This is an interactive process as well for the user on the client device 106. The grid could be presented with varying patterns, colors, and so forth, based on user input and response to stimuli. Current perimetry devices use circular light stimuli of different contrast and intensity to interrogate the perimetric map of a patient's visual function. But such stimuli cannot detect metamorphopsias and subtle changes and defects as is the case with diseases like macular degeneration. In the macular perimetry test disclosed herein as shown in FIG. 3, a grid pattern 308 is shown in the central 15 degrees from the central fixation point in order to find metamorphopsias. Grid boxes 310 with 2-12 quadratic elements light up in sequence and the patient clicks or provides user input only when there is an abnormality. More or less elements are also contemplated.

In addition to the macular grid perimetry, photoreceptor bleaching and saturation can be employed to further enhance the expression of subtle defects. This is achieved by having the screen 118 turn from dark background to bright white background and flash multiple times while the grid is displayed. This photoreceptor bleaching creates a grid after-image which further augments any hidden defects. The patient can provide their feedback on their client device 106 in any modality regarding the grid after-image. The feedback can be evaluated by the cloud environment 102 for determining defects.

Another aspect of this disclosure relates to the videokeratoscopy test module 140 configured on the cloud environment 102 to provide remote unaided videokeratoscopy using a known image pattern like a placido disk or any image form to capture its reflection off the ocular surface. Keratoscopy is a method to detect and define abnormalities in the smoothness or curvature of the cornea or ocular surface based off the reflected images that are presented to the eye. For example, if a series of concentric circles of varying diameter, from large to small, is presented on a monitor like an iPad or desktop monitor, any abnormal curvature of the cornea such as an elongated cornea will cause distortions in the pattern of the concentric circles that are reflected from the cornea or ocular surface. Different types of image pattern can be used from grids to circles and other geometric shapes can be used as a test pattern. The reflected image is analyzed by mathematical and statistical models that can be further aided with an artificial intelligence implementation. Abnormalities in the stability of the tear film will also produce changes in the reflected image, which can be used to assess for dry eye, in additional to other uses of keratoscopy for the diagnosis of keratoconus, Terrien's marginal degeneration, LASIK associated corneal decompensation, or other corneal and ocular surface abnormalities. It also aids in the treatment with and management of contact lens or scleral lens fitting. This is shown by way of example in FIG. 4.

Figure 4:
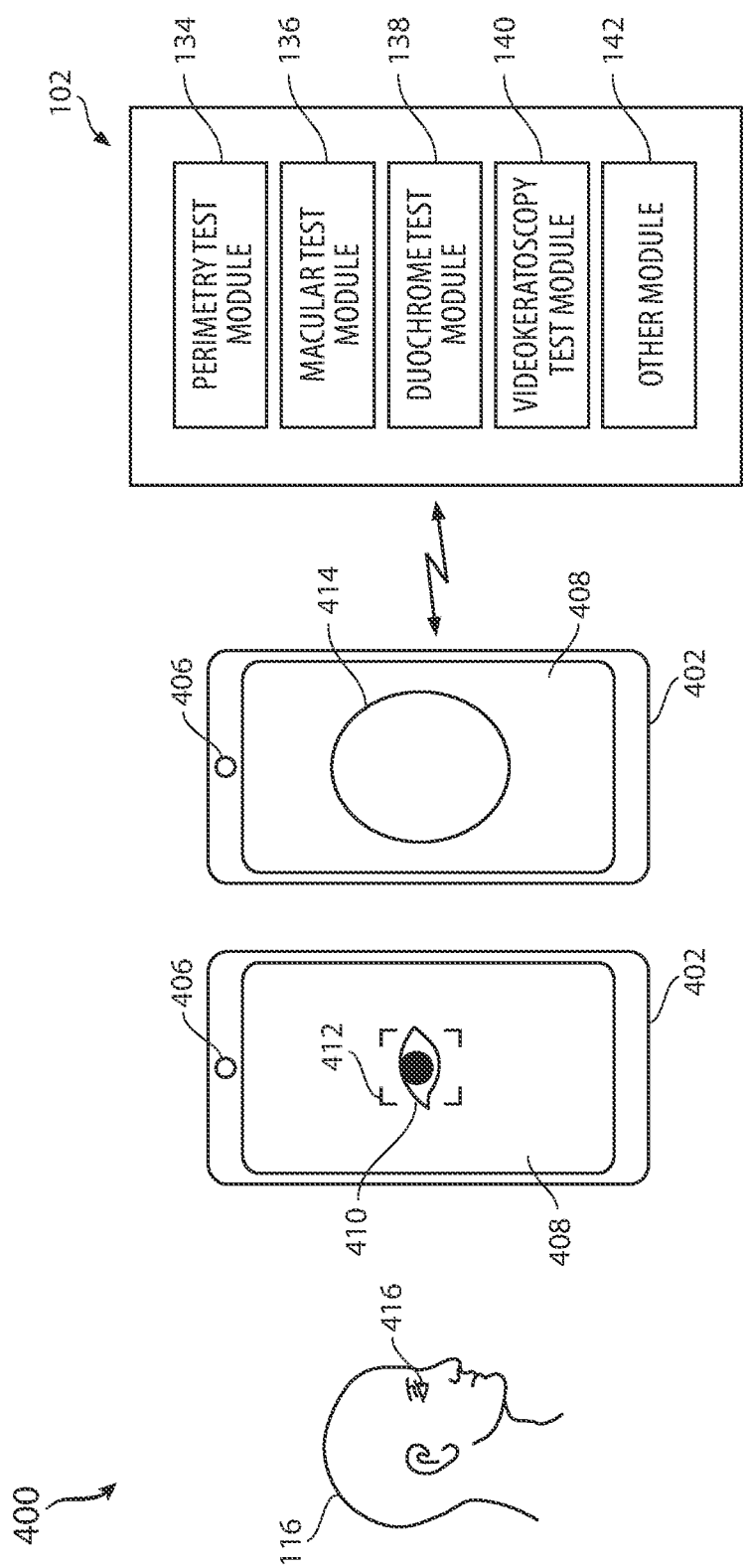
FIG. 4 illustrates a particular test in which the patient positions their eye or eyes close to a display of the client device.

Dynamic-area high-speed videokeratoscopy (DA-HSV) represents an established method for the assessment of the tear film surface quality (TFSQ) using placido-disk videokeratoscopy for corneal topography assessment. In this technique, a circular light pattern (Placido Disk) 414 is projected on the cornea surface and its reflection is assessed for corneal topography as well as tear film stability using image processing. Currently all HSV devices are non-virtual, expensive hardware equipment installed in the doctor's offices which require a technician for operation. Herein is disclosed a self-imaging method and system to allow patients participate in this test using their portable electronic device such as smart phone 106/402. As shown in FIG. 4, the method can utilize a front-facing camera 406 of a smart phone 402 and a simultaneous placido ring 414 displayed on the screen 408. The camera does not necessarily have to be front-facing but can face a different direction as well. The camera 406 may also be from a separate device positioned to be able to view the eye. When the eye 410 of the patient 116 is centered 412 appropriately with the camera 406, a placido ring element(s) 414 (or other corneal reflective light pattern) is displayed on the phone screen 408 so that it is reflected on the cornea surface. Simultaneous imaging with photography and/or videography is carried out to capture the corneal reflections which are than stored and analyzed using image processing and analysis either on the phone or client device 402 or a cloud environment 102. Any distortions of the placido corneal reflections are analyzed for presence of astigmatism, corneal abrasion, ocular surface disease and problems such as dry eye. The positioning of the head can be guided by the module 140 to help the person be properly positioned for the system to receive the reflective light pattern off of the cornea surface. For example, based on feedback data, the system might indicate to the user "lower your phone about 1 inch", or "move the phone to your right ½ inch". The user may be asked to pass the phone across the eye left and right and/or up and down to capture different positions of the light source and thus reflective patterns off of the cornea surface not just recognize a person's face but determine the position of the face, distance from the camera, and so forth.

3D Depth-sensing, oculocephalic scan-and-track telehealth videokeratoscopy and ocular surface and periorbital topography testing can also be implemented via consumer electronic device including a mobile device 402. A digital videokeratoscopy and ocular topography ophthalmic diagnostic test as described previously can be enhanced with a one or more 3D depth scanning camera(s) on a monitor, mobile device or screen (such as TrueDepth (TD), Time-Of-Flight (TOF), LIDAR, sonar, ultrasonic or other sensor on a device, including AI enhanced 3D depth sensing extrapolations and enhancements of the above as well as regular cameras) can be used for high-precision topography and imaging of the tear film, conjunctiva, cornea, lid margin and periocular and periorbital areas, including facial epidermal and dermal imaging of surface lesions. This can include imaging macular and popular lesions as well as aesthetic aging topographic dermatologic changes. Ocular surface topography obtained by such scans can be used for imaging, diagnostics and monitoring of keratoconus, dry eye, tear film, pterygium, corneal ulcers, conjunctival hyperemia and lesions, and other identifiable ocular surface pathology where high-precision topographic scanning adds clinical utility. The data for 3D depths sensing can also be combined with 2D photographic data to increase granular details to provide even more precise analysis.

In one aspect, the 3D renderings on a device could be used to guide the user in moving the device around to certain positions such that the topographical imaging could be fully captured. A 3D image could be presented and the user could be asked to find an object or keep the 3D image configured such that the column is only seen from a top side and not an angled side, or any 3D image and guidance could be provided to aid the user in having a more comfortable experience when taking any of the eye tests described herein. As a user moves their head around, the depth sensor on a mobile device, for example, can use its 3D depth sensor to map out or image aspect of the eye as described above.

In one aspect, controlling the user's head position can be a coordinated effort between a first device with a camera for taking images of their eye, and a second device 402 that is used to present the placido disk 414. The coordination can be via Bluetooth or other wireless protocol between the two devices or the coordination can occur via the cloud-based environment 102.

In another aspect, facial recognition capability on a device can be implemented to help position the patient's eyes. A facial recognition algorithm can be modified and used for positioning purposes. Currently, for example, on an iPhone, the facial recognition does not take into account a particular position as long as the user is generally in the range or region to have their face recognized. The data however could be used for positioning purposes to take the respective eye tests disclosed herein. Thus, a visual testing application could access the facial recognition features of a device and utilize the data, modify its operation, and so forth, to utilize the facial recognition feature to achieve face positioning.

Note that in one scenario multiple steps might need to be taken to properly place the eye 410 in the right position of the display 408. For example, typically when a user places their phone 402 in a "selfie" mode such that the camera 406 on the front side of the phone 402 is used, the image on the screen 408 is taken from the camera 406. However, the above approach can involve a multi-step process. For example, when this test or functionality is initiated, a first step can involve placing the phone 402 in a proper state to be able to lead the user in positioning their eye 416 in the right spot 410 relative to the camera 402 and the display 408.

An application, an "app clip" from a company like Apple, or functionality provided via a browser interface with the cloud environment 102 can cause the phone 402 to be placed in this state. Obtaining the proper state might involve selecting a telephoto mode or portrait mode for the camera 406 rather than a wide angle mode. Any mode can be chosen for improved imaging in a particular test. Obtaining the proper state might include selecting from a plurality of cameras on the phone 402 such that the proper camera is selected for the test.

In an alternative, rather than choosing from selfie, portrait, wide angle, narrow angle, etc., modes on the phone, a specific mode can be generated or configured for use in these types of tests. A special eye test mode could be added to the plurality of available modes and which would be focused on high quality images or video, close up views of the eye, face-positioning assistance features, auto-stability features, as well as stimulus features whether through the display or from a flash. For example, a flash might be altered to provide a ring of light rather than the traditional circular image of light.

Thus, a first phase might involve establishing the phone 402 in the proper state for the test in which the camera 406 presents on the display 408 the image that it sees to lead the user in positioning 412 their eye 416 in the proper place. Once completed, which can be determined as detected by the phone 402, a second phase can be initiated in which the display 408 no longer presents what is being seen by the camera. The display of the phone in this phase presents the placido ring 414 displayed on the screen 408 and that utilizes the camera 406 for detecting reflections off of the eye 416 of the user 116. The flash or flashlight feature might also be adjusted to present a ring rather than the normal circular shape. Data received by the camera 406 with respect to reflections off of the item 416 of the placido ring 414 can be transmitted to the cloud environment 102 for evaluation via a machine learning algorithm or some other approach such as direct viewing by a doctor. Data about the eye can also be gathered from a separate device and camera as well and transmitted to the cloud environment 102. Images, video, or other data can also be transmitted to the cloud environment 102 for analysis. In this two-phased approach, the user is properly positioned and then the device presents the placido ring or other relevant geometric patterns 414 for reflection off of the user's eye. The reflection is received by the camera 406 (or a separate device) for sending to the cloud environment 102 for analysis.

In another aspect, the user may be instructed to position their eye 416 relative to the phone 402 and then once the device presents the placido ring 414, the user might be instructed visually or audibly to move their phone 402 in a certain rotation or to certain positions such that a different reflection of the placido ring 414 can be recorded by the camera 406 and transmitted to the cloud environment 102. In this manner, different views can be recorded of the patient's eye 416 and used to evaluate its condition. Audio, haptic, or visual instructions can be presented to the user with respect to whether to move up, tilt left, or otherwise to move the camera around. Sensors on the mobile device 402 can be used to provide feedback regarding the current position or orientation of the device 402 to aid in providing the proper instructions. Instructions can also be sent to a companion device held by a person there with the patient taking the test to help them make the proper movement in position. Images, audio, video, and so forth could be presented on a companion device to help instruct the patent regarding what they need to do. The instructions might also be provided not just for the device 402 showing the placido disk 414 but for another camera that is used to take images of the eye 416.

The algorithm can use the screen resolution as a reference point to determine the proper position of the user. In one aspect, the cloud environment 102 can retrieve the screen resolution of the client device 106/402 and based on that data can adjust a positioning algorithm to adjust a placido ring 414 or other visual queue to properly position the user's head 116 for the test. The cloud environment 102 can make adjustments on the algorithm with respect to how to instruct or help the user to position themselves properly. Such a positioning is used in preparation for the virtual perimetry or other visual testing disclosed herein.

The cornea of the eye is 10-12 millimeters. The camera 108 or algorithm can use the size of the cornea as received at the camera 108 as a reference point to identify how far away the user is from the screen 118. The user head or eyes are fit into a particular outline or position and can help the user be positioned properly. In one aspect, where a user has downloaded an application or is using an "App Clip" (a feature provided by Apple for a portion or snippet of code for a particular function rather than an entire application) or other computer code, this function could be performed locally to detect an eye position and size, based on the screen size and resolution, instruct the user to fit their head or eyes in an outline 122. Other methods could also be used to determine distance.

During a visual test, if the user is in the right position, they will have a natural blind spot in their field of vision. This is the spot on their optical nerve that connects to the retina and has no light-sensitive cells. One technique for insuring that the user remains in the proper position through the test is to present a light stimulus in the user's blind spot and if they move, they will be able to see the light (and may thus respond indicating that they see that particular stimulus). At this point, the user will have to move back into proper position such that the light stimulus disappears. Such user input might trigger, for example, the cloud environment 102 to initiate the virtual technician 132 or notify a live technician who can instruct the patient to focus on the proper spot 120 and continue the test.

During a test, the cloud environment 102 can use machine learning algorithms to determine if the user has moved, and can return and instruct them to maintain their position throughout the test. The cloud environment 102 may present the outline or overlay 122, which was previously used to position the user, during the test to return them to the proper position. For example, a dim version of the outline 122 may be presented while the test is going on to remind the user of the proper position. The purpose of this outline 122 will be to remind them or correct their position. The presentation of this outline 122 during the test can be triggered by input about the user during the test that is received by the cloud environment 102. Any data is received by the cloud environment 102 can be utilized by an algorithm, which can include a machine learning or trained algorithm, which can evaluate that data to determine or classify that the user has moved out of a proper position during the test. Thus, data related to the user's blind spot, response time, response accuracy, position of the patient eyes or head as viewed by a camera 108, and so forth can be evaluated to determine whether to present the image 122 which can guide the user regarding their head position. Presenting the outline 122 can also be connected with the use of a virtual or real technician 132 which can guide the user regarding what needs to be done. For example, if this operation is triggered, the system may initiate a virtual technician 132 while presenting (during the test) the outline 122 such that the user can be instructed to reposition their head within the outline. In another aspect, the test can maintain a faint outline 122 throughout the test that enables the user to monitor themselves to remain in the proper position. A gamification approach can also be used to give the patient points or rewards to maintaining a proper position in the outline 122 throughout the test. In yet another aspect, the visual configuration can be adjusted when the user moves their eye focus such that they see the spot which usually is in their natural blind spot. The blind spot can move to always be within the natural blind spot and the rest of the display can also move in a corresponding way to continue the respective test.

In another aspect, this disclosure can utilize white or colored patterns or images on the screen 408 of a mobile, hand-held or computer device 402 with a front-facing camera 406 or camera facing a different direction. Such patterns 414 can include rings, rectangles, linear or other geometric elements or shapes of various size, color(s), or configuration necessary to generate a corneal/conjunctival reflection and/or projection with 0.1-30 mm discrete pattern resolution within the focal plane of a camera placed at 1"-3' from the eye 416. Thus, the pattern 414 shown is illustrated by example only and other patterns with different color configurations as described above can also be used. The camera 406 (or a separate camera) can capture the reflected image on the ocular surface and image processing on the device 402 and/or on the cloud environment 102 can analyze the pattern and/or reflectivity of reflected images for changes. Dry eye increases the instability of the tear film that covers the ocular surface, and this instability will affect the pattern and reflectivity of the images over time. Analysis of the dynamic changes in reflected images over time provides a useful and novel qualitative and quantitative method for dry eye assessment. There have been a number of methods for dry eye analysis without contact. Most methods require the use of aberometers, interferometers, optical coherence tomographers or other specialized equipment for image acquisition and analysis. See, for example, U.S. Pat. No. 6,299,305 that uses fluorescein dye+interferometer, U.S. 2008/0273171 that uses an interferometer, U.S. Pat. No. 10,244,939 from TearScience that uses a specialized apparatus, U.S. Pat. No. 10,376,140 from J&J that uses an interferometer, and U.S. Pat. No. 10,285,582 that uses a two-camera system. Each of these documents is incorporated herein by reference.

In addition to capturing the reflection of the light elements on the cornea, the test also can capture blink dynamics and its effect on the ocular surface reflection during the test. Blink dynamics include rate of blink, speed of blink, duration and completeness of blink as well as the reflection of the adjacent ocular surface before, during and after a blink. Furthermore, pupillary changes in response to light effect from the screen presentation pattern can be captured by the camera to evaluate pupillary response and dynamics unilaterally or bilaterally.

Figure 5:
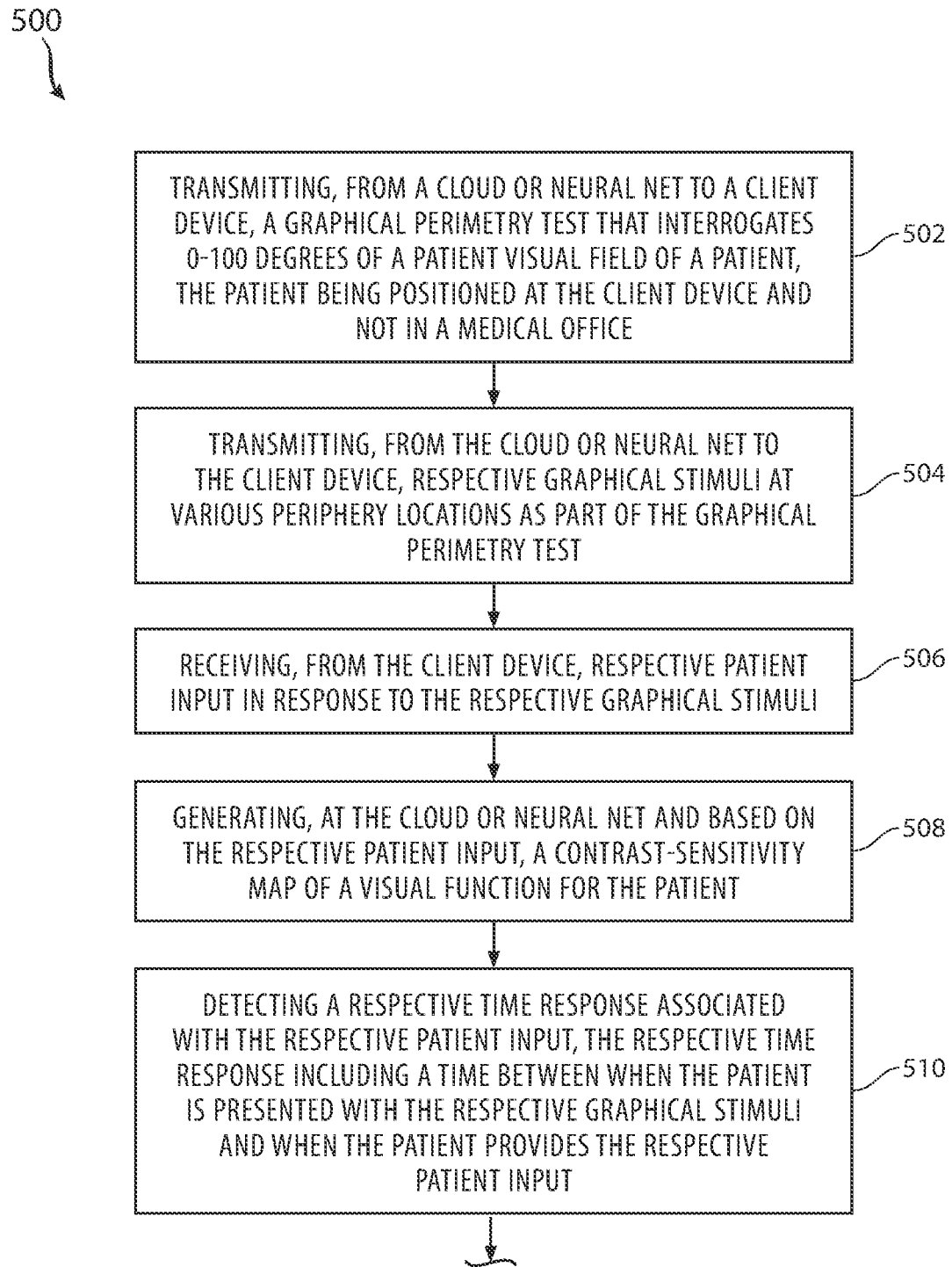
FIG. 5 illustrates an example method related to developing a contrast-sensitivity map.
Figure 5:
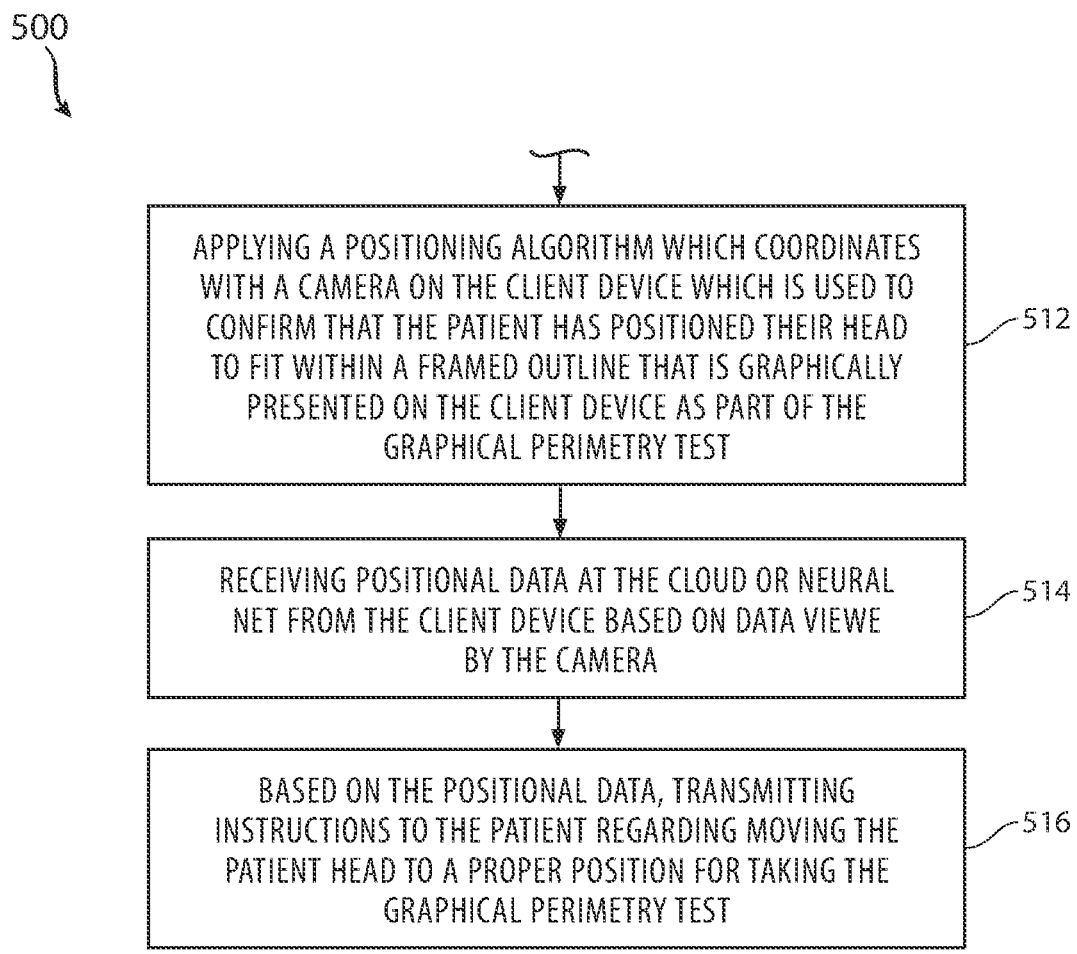

FIG. 5 illustrates an example method 500 which relates to the perimetry module 134. The method 500 includes transmitting, from a cloud or neural network to a client device, a graphical perimetry test that interrogates 0-100 degrees of a patient visual field of a patient, the patient being positioned at the client device and not in a medical office (502). The cloud environment 102 can be a neural network, a network-based server which is positioned on the Internet or a cloud-based environment and which transmits the user interface, information, or other data to the client device to carry out the ocular test. The client device 106 can be a client device that is typically used by the patient for other uses such as surfing the Internet, checking email, working on documents, editing images or videos, and so forth. The client device is typically not a specialized medical device as would be used in a doctor's or medical office for providing ocular tests. The graphical perimetry test can include an animated element 120 which enhances patient concentration and maintains gaze direction of the patient. The animated element 120 can be presented in a continuously dynamic manner, meaning that it is not presented for a defined period of time as a static image and then changed to an altered image for a period of time. The animated element 120 in one aspect can be continuously moving as an animation would such as cartoon or a movie. The method can include transmitting, from the cloud environment or neural net 102 to the client device 106, respective graphical stimuli 120 at various periphery locations as part of the graphical perimetry test (504), receiving, from the client device, respective patient input in response to the respective graphical stimuli (506) and generating, at the cloud or neural net and based on the respective patient input, a contrast-sensitivity map of a visual function for the patient (508). The cloud environment 102 can interrogate the client device 106 for data such as display characteristics (size, pixel count, etc.) or other characteristics in order to tailor the visual tests to the specific client device capabilities.

The animated element 120 can include a gamification approach to presenting the animated element or even to participating and responding to stimuli. For example, a gamification approach might include presenting the patient with tokens or credits for each period of time that they are determined to be staring at the animated element properly or for each input response to stimuli. For example, if a user stares for 3 minutes or responds to 10 light stimuli in a row, the user might receive a discount, token, or some other benefit for their good behavior during the test.

The animated element 120 can be positioned in a middle portion of the graphical perimetry test. The graphical perimetry test can represent an emulation of an office-based perimetry test. In office-based perimetry tests, there is no animated element that the user watches to maintain their focus as usually there is a doctor or technician that is personally right there with the patient helping them to remain focused. However, since the patient is at home in the context described herein, modifications need to be made to the graphical presentation that the user will be viewing on their own client device in order to help or assist the patient to maintain focus.

The method can further include detecting a respective time response associated with the respective patient input, the respective time response including a time between when the patient is presented with the respective graphical stimuli and when the patient provides the respective patient input (510). The respective time response can be used to generate the contrast-sensitivity map or can be used to detect other medical conditions or probe how patients are responding to treatment of other medical conditions as well.

The method can further include applying a positioning algorithm which coordinates with a camera on the client device which is used to confirm that the patient has positioned their head to fit within a framed outline that is graphically presented on the client device as part of the graphical perimetry test (512). The positioning algorithm can aid the patient in positioning their head a certain distance from a display on the client device.

In another aspect, the method further includes receiving positional data at the cloud or neural net from the client device based on data viewed by the camera (514) and, based on the positional data, transmitting instructions to the patient regarding moving the patient head to a proper position for taking the graphical perimetry test (516). The method can also include presenting an embedded virtual technician which the patient can access during the graphical perimetry test. The graphical perimetry test can combine and integrate online visual acuity testing, color vision testing and central macular function testing along with testing perimetry for the patient.

An example system can include a processor and a computer-readable storage device storing instructions which, when executed by the processor, cause the processor to perform operations including transmitting, to a client device, a graphical perimetry test that interrogates 0-100 degrees of a patient visual field of a patient, the patient being positioned at the client device and not in a medical office. The graphical perimetry test can include an animated element which enhances patient concentration and maintains gaze direction of the patient. The operations can include transmitting, to the client device, respective graphical stimuli at various periphery locations as part of the graphical perimetry test, receiving, from the client device, respective patient input in response to the respective graphical stimuli and generating, based on the respective patient input, a contrast-sensitivity map of a visual function for the patient. Any of the functions or operations disclosed herein can be performed by the system having a programmed module with computer-readable instructions for controlling the processor or the computing device. Embodiments of the disclosure can also be claimed from the standpoint of the client device as well and would encompass the series of operations or steps that are performed by the client device such as receiving the perimetry test from the server and receiving patient input unit or device such as a mouse or keyboard of the client device.

In another example, all of the functions disclosed herein as being performed by the cloud environment 102 can be performed by the client device 106. An application can be downloaded such that the testing and evaluation can be performed at least in part on the client device 106 via the application, an App Clip, or browser-based functionality. In this case, any action performed by the server (transmitting, receiving data, evaluating, etc.) can equally be performed via the application, App Clip or browser-based processing on the client device. In other cases, some evaluation such as the timing between presenting stimuli and receiving responsive user input can be performed via an application, App clip or browser-based processing, while the machine-learning-based algorithm operation can be performed by the cloud environment 102.

Figure 6:
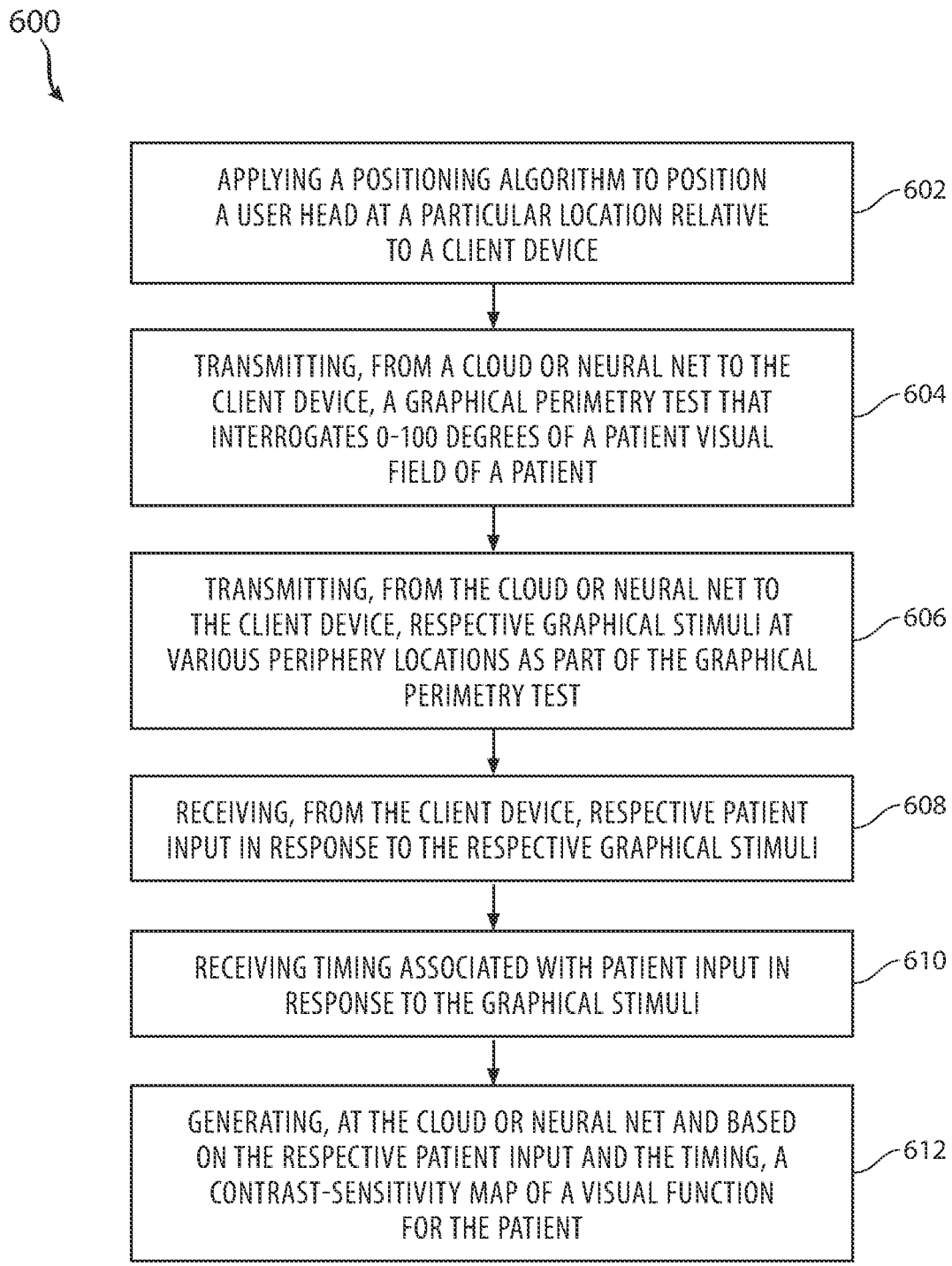
FIG. 6 illustrates another example method related to developing the contrast-sensitivity map.

FIG. 6 illustrates another example method 600 related to a positioning algorithm. The method 600 includes applying a positioning algorithm to position a user head at a particular location relative to a client device (602), transmitting, from a cloud or neural net to the client device, a graphical perimetry test that interrogates 0-100 degrees of a patient visual field of a patient (604), transmitting, from the cloud or neural net to the client device, respective graphical stimuli at various periphery locations as part of the graphical perimetry test (606), receiving, from the client device, respective patient input in response to the respective graphical stimuli (608), receiving timing associated with patient input in response to the graphical stimuli (610), and generating, at the cloud or neural net and based on the respective patient input and the timing, a contrast-sensitivity map of a visual function for the patient (612).

Figure 7:
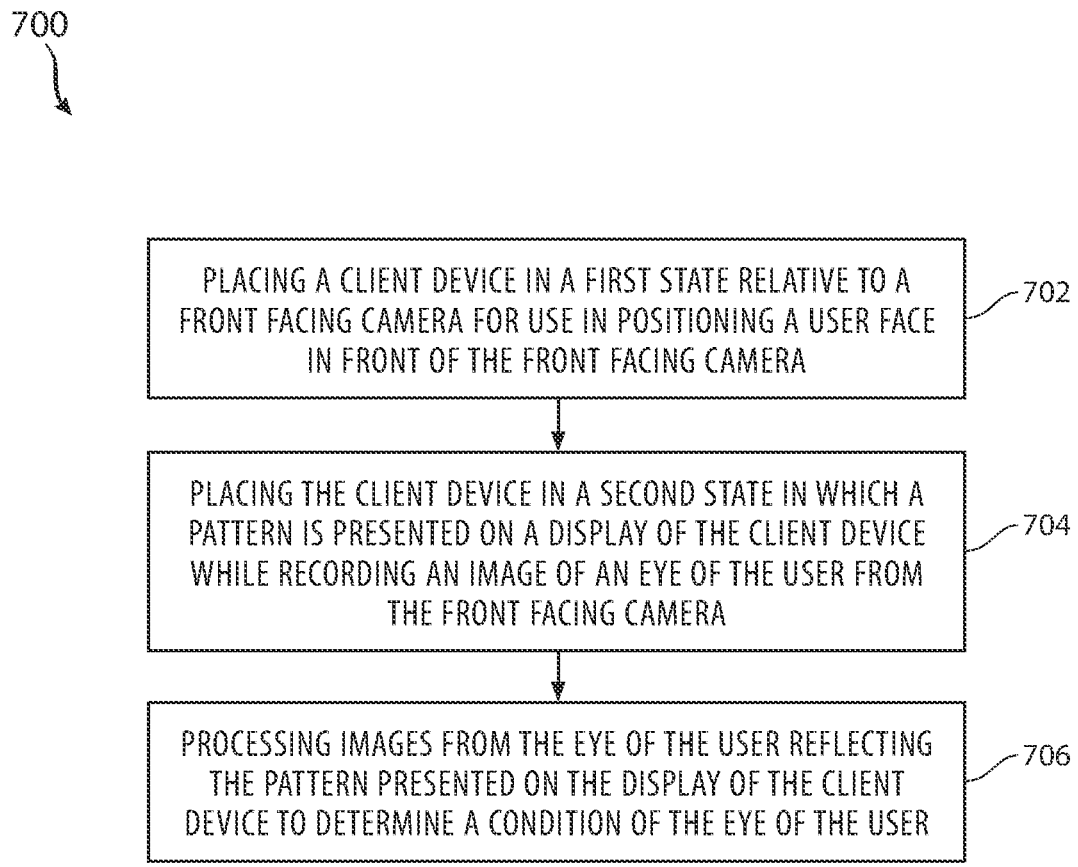
FIG. 7 illustrates an example method related to a reflecting patterns off the eye to determine the eye condition.

FIG. 7 illustrates another method 700 of this disclosure. This method is practiced in the context of a client device 106 and a cloud environment 102 as shown in FIG. 1. The method includes placing a client device in a first state relative to a front facing camera for use in positioning a user face in front of the front facing camera (702), placing the client device in a second state in which a pattern is presented on a display of the client device while recording an image of an eye of the user from the front facing camera (704), processing images from the eye of the user reflecting the pattern presented on the display of the client device to determine a condition of the eye of the user (706). As noted above, this approach can be performed in several phases using the camera of a mobile device and the display to first position the user properly and then present the pattern to be reflected off the user's eye and received by the camera for transmission and evaluation.

Figure 8:
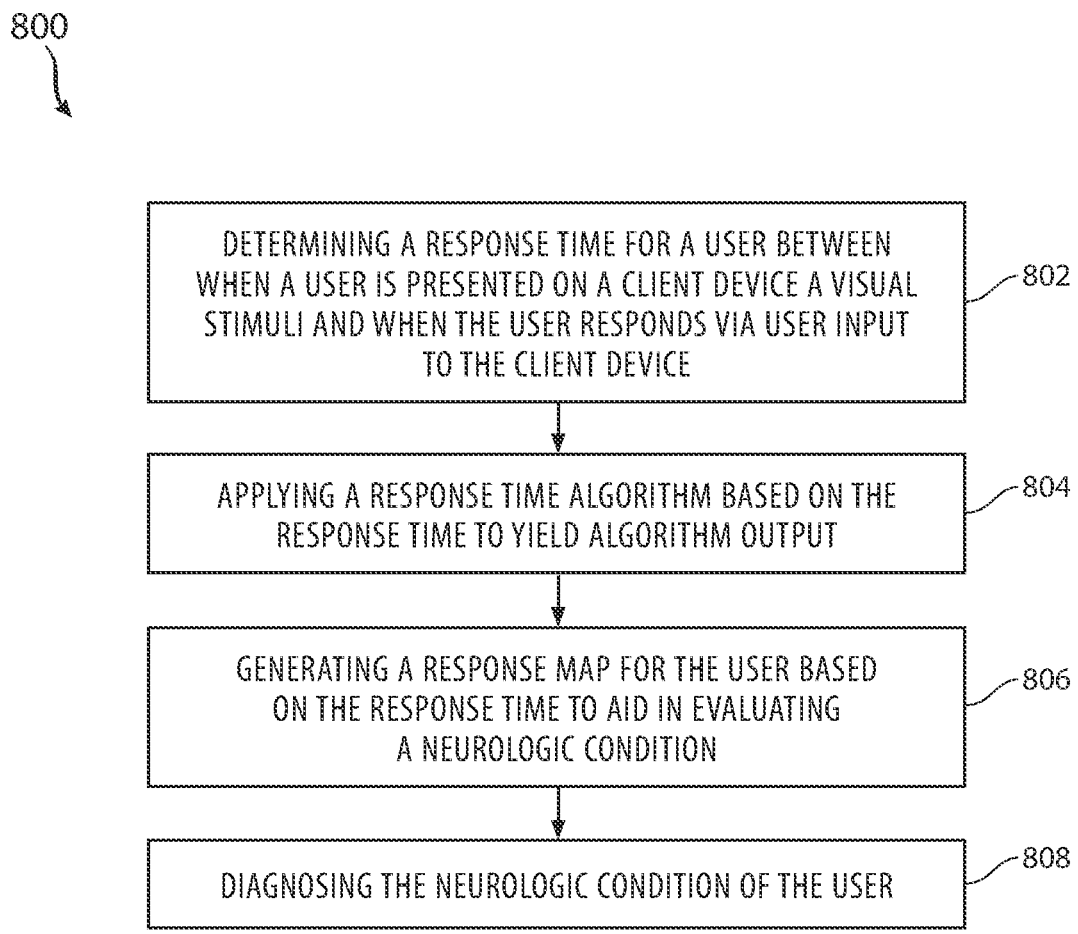
FIG. 8 illustrates an example method related to evaluating a response time to stimulus for a user.

FIG. 8 illustrates an example method 800 according to an aspect of this disclosure related to user response times to presented stimuli. This method is practiced in the context of a client device 106 and a cloud environment 102 as shown in FIG. 1. The method includes determining a response time for a user between when a user is presented on a client device a visual stimuli and when the user responds via user input to the client device (802), applying a response time algorithm based on the response time to yield algorithm output (804), generating a response map for the user based on the response time to aid in evaluating a neurologic condition (806) and diagnosing the neurologic condition of the user (808).

Figure 9:
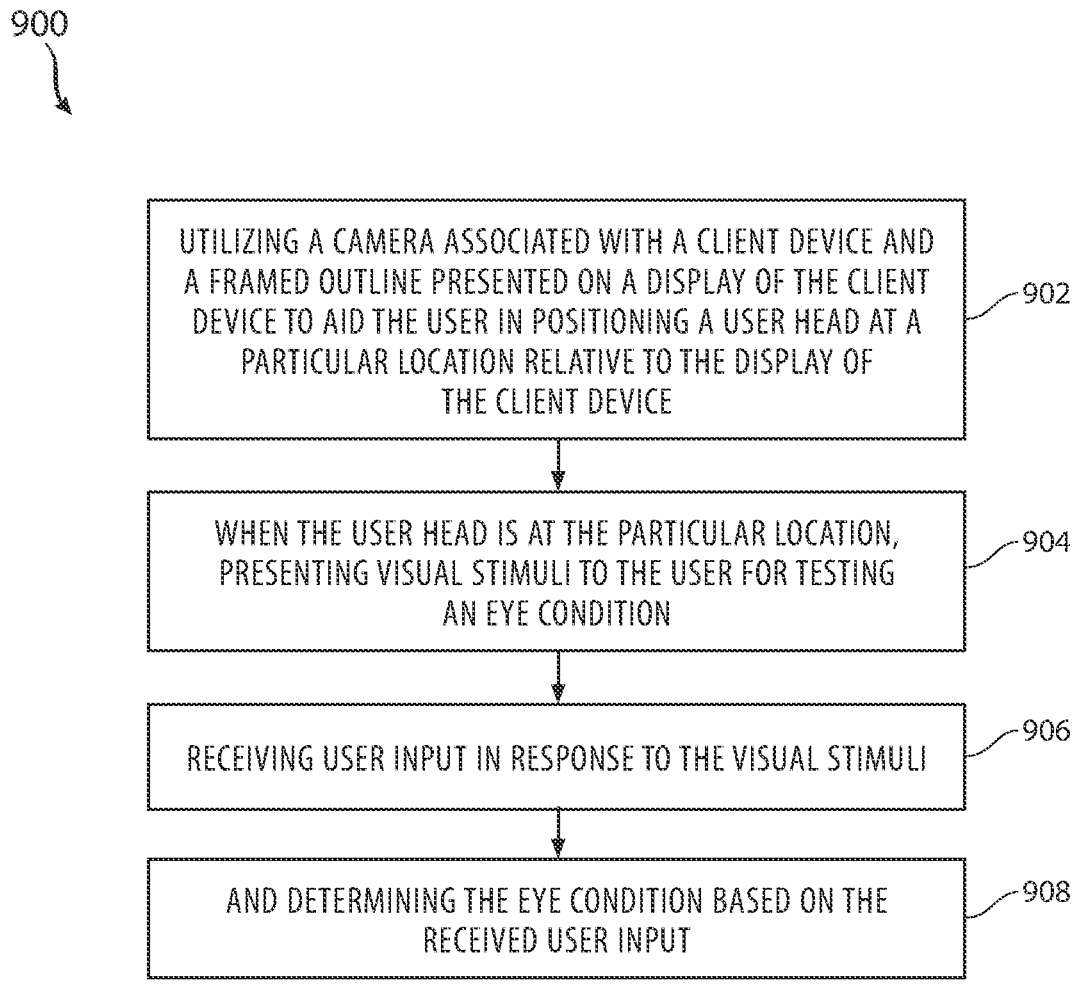
FIG. 9 illustrates an example method related to determining an eye condition based on user input in response to visual stimuli.

FIG. 9 illustrates another method 900 according to an aspect of this disclosure. This method is practiced in the context of a client device 106 and a cloud environment 102 as shown in FIG. 1. The method includes, utilizing a camera associated with a client device and a framed outline presented on a display of the client device to aid the user in positioning a user head at a particular location relative to the display of the client device (902), when the user head is at the particular location, presenting visual stimuli to the user for testing an eye condition (904), receiving user input in response to the visual stimuli (906), and determining the eye condition based on the received user input (908). The algorithm can use the screen resolution or the screen size or other parameter associated with the client device 106 as a reference point to determine the proper position of the user. The cornea of the eye is 10-12 millimeters. The camera or algorithm can use the size of the cornea as a reference point to identify how far away the user is from the screen. The user head or eyes are fit into a particular outline or position and can help the user be positioned properly.

In one aspect, the user might have a mobile phone and given the resolution and/or the size of the phone, the cloud environment 102 may instruct the user to turn the mobile device 106 vertically or horizontally in order to take the test. Part of the test may involve the mobile device 106 in a horizontal direction and another part of the test may require the device to be in a vertical direction.

Figure 10A:
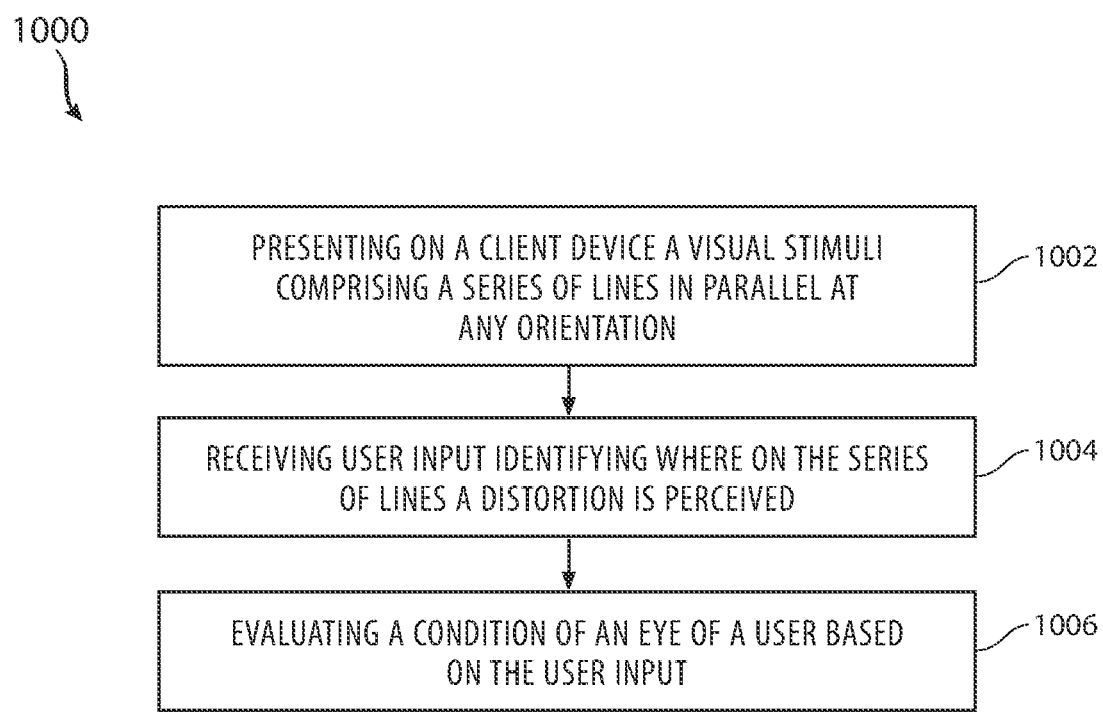
FIG. 10A illustrates an example method related to presenting parallel lines to a user to evaluation an eye condition.

FIG. 10A illustrates an example method 1000 according to an aspect of this disclosure particularly related to the macular text module 136. This method is practiced in the context of a client device 106 and a cloud environment 102 as shown in FIG. 1. The method includes presenting on a client device a visual stimuli comprising a series of lines in parallel at any orientation (1002), receiving user input identifying where on the series of lines a distortion is perceived (1004), and evaluating a condition of an eye of a user based on the user input (1006). The lines can be presented in a group and may be presented, for example, one or two at a time in various locations to probe the user's ability to see clean lines in particular locations. Typically as noted herein the lines are presented on a user device and not on a specialized medical device in a doctor's office.

Figure 10B:
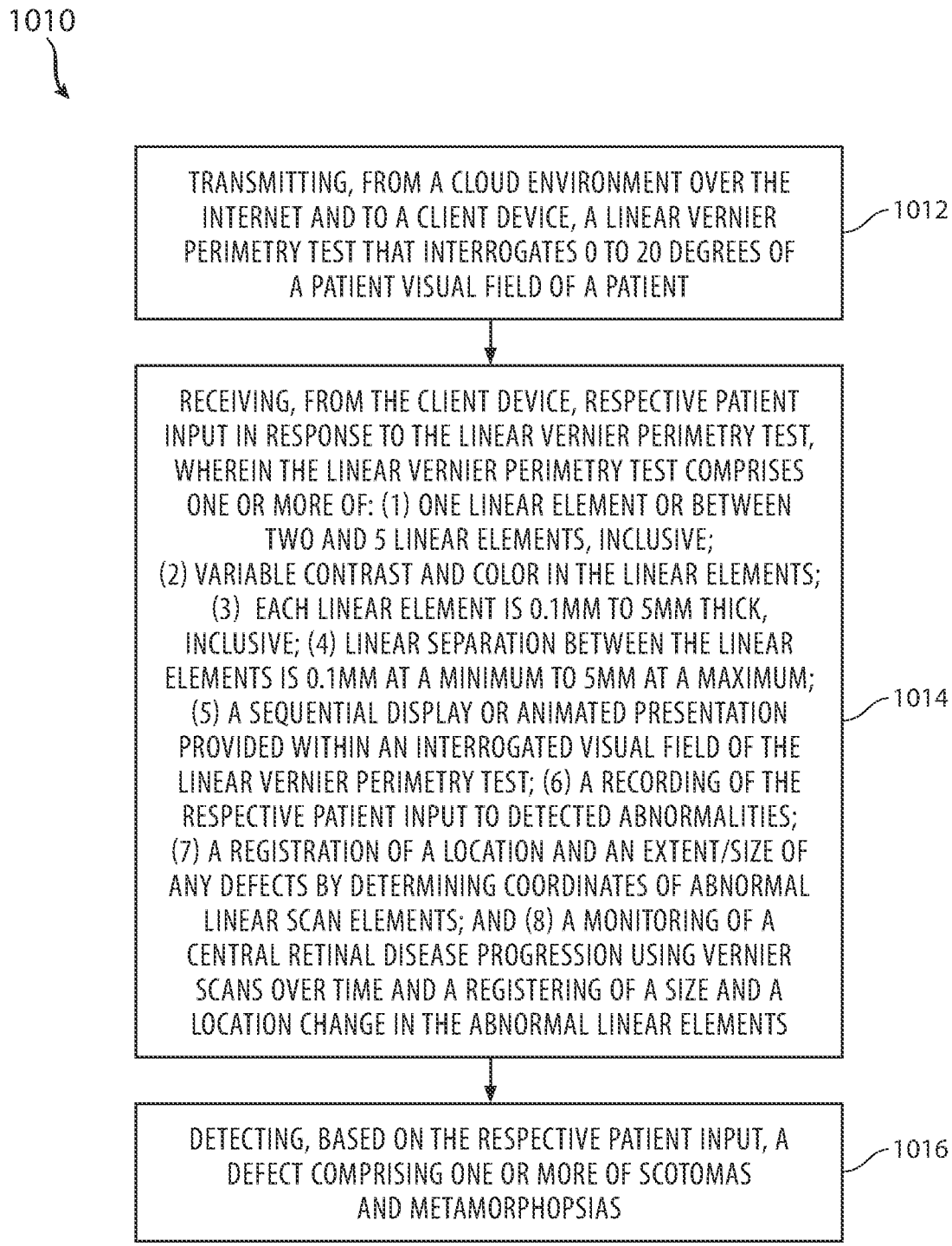
FIG. 10B illustrates an example method related to linear elements to a user to evaluation an eye condition.

FIG. 10B illustrates an example method 1010 related to using a linear Vernier perimetry test. The method 1010 can include transmitting, from a cloud environment over the Internet and to a client device 106, a linear Vernier perimetry test that interrogates 0 to 20 degrees of a patient visual field of a patient (1012), receiving, from the client device, respective patient input in response to the linear Vernier perimetry test, wherein the linear Vernier perimetry test comprises one or more of: (1) one linear element or between two and 5 linear elements, inclusive; (2) variable contrast and color in the linear elements; (3) each linear element is 0.1 mm to 5 mm thick, inclusive; (4) linear separation between the linear elements is 0.1 mm at a minimum to 5 mm at a maximum; (5) a sequential display or animated presentation provided within an interrogated visual field of the linear Vernier perimetry test; (6) a recording of the respective patient input to detected abnormalities; (7) a registration of a location and an extent/size of any defects by determining coordinates of abnormal linear scan elements; and (8) a monitoring of a central retinal disease progression using Vernier scans over time and a registering of a size and a location change in the abnormal linear elements (1014) and detecting, based on the respective patient input, a defect comprising one or more of scotomas and metamorphopsias (1016). The operations can be programmed and implemented as part of one or more modules including the macular test module 136. The operations can also be performed as has been noted herein by a downloaded application on a local client device and not transmitted over the Internet. Thus, the linear Vernier perimetry test can be presented by a local application and the results can be reported back to a network-based or cloud-based environment 102 for analysis and reporting.

Figure 11:
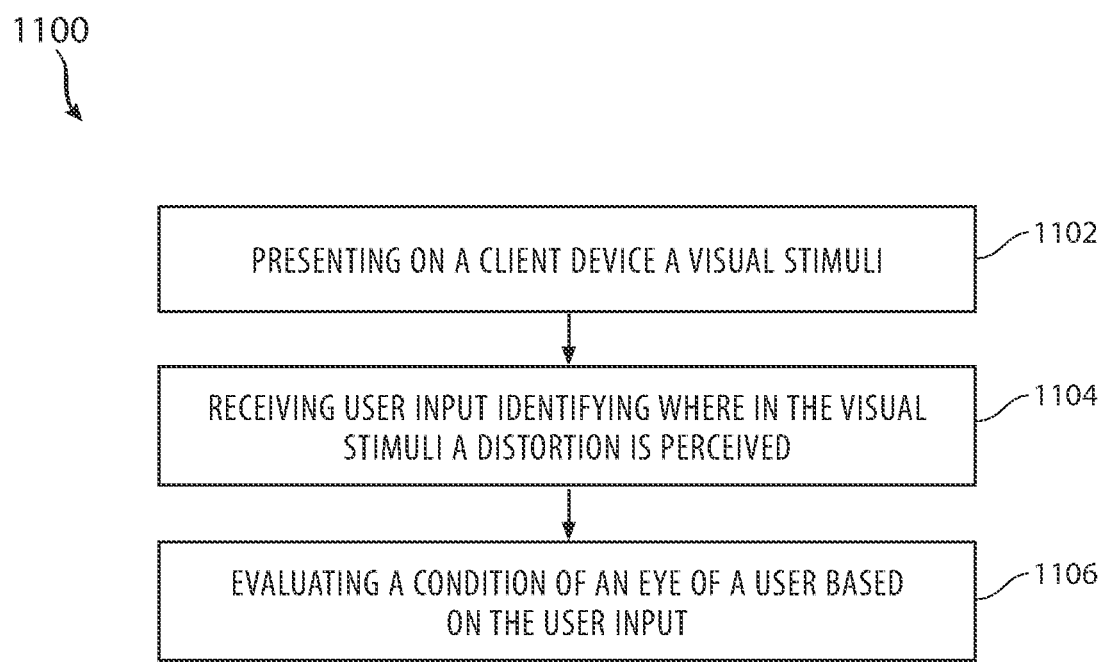
FIG. 11 illustrates an example method of providing visual stimuli and receiving user input identifying where the visual stimuli is distorted.

FIG. 11 illustrates an example method 1100 according to an aspect of this disclosure. This method is practiced in the context of a client device 106 and a cloud environment 102 as shown in FIG. 1. The method includes presenting on a client device a visual stimuli (1102), receiving user input identifying where in the visual stimuli a distortion is perceived (1004), and evaluating a condition of an eye of a user based on the user input (1006). The visual stimuli can be a grid pattern, a red/green background with varying brightness, circles, other shapes, a circular light stimuli of different contrasts and intensity and so forth. The visual stimuli can be dynamic or static.

Figure 12:
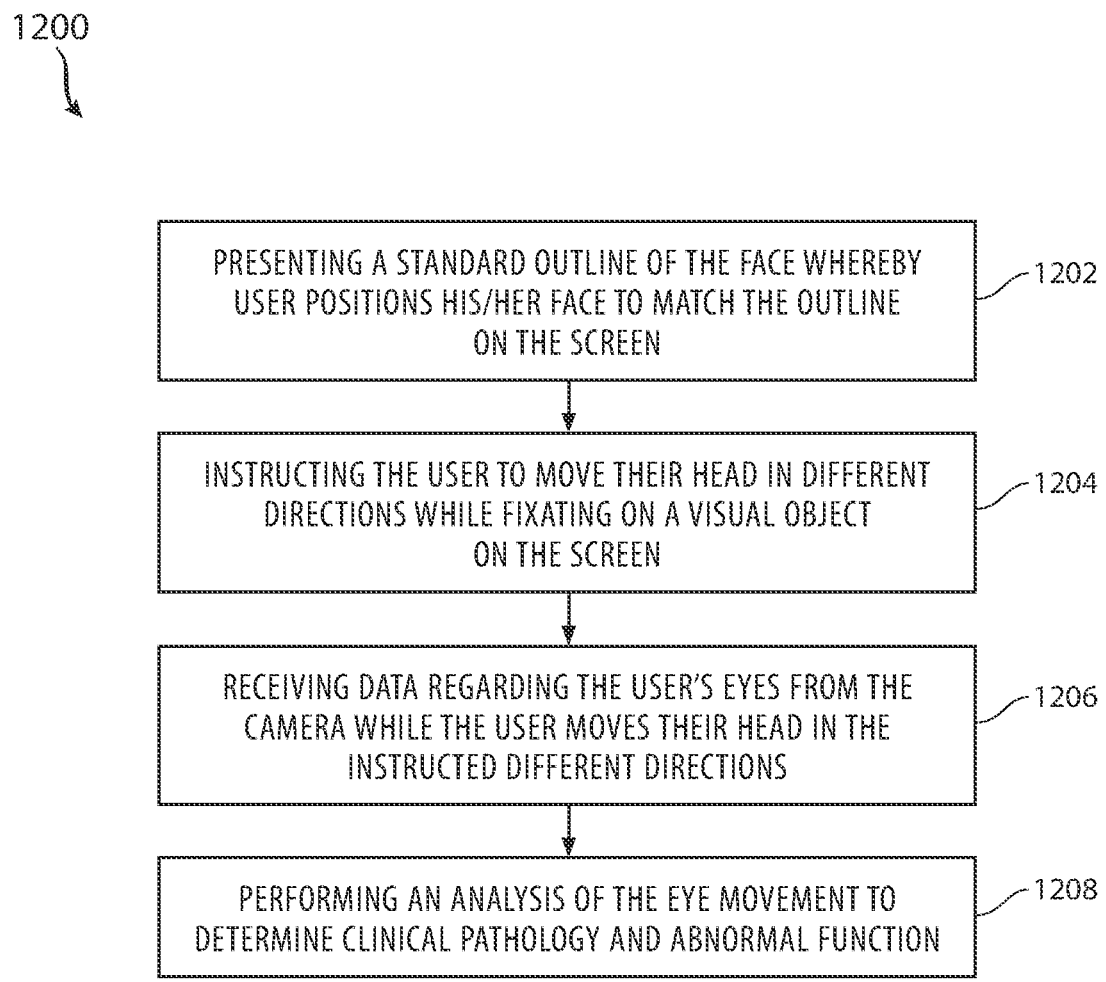
FIG. 12 illustrates an example method related to receiving data about a user's eyes based on their head movement in connection with detecting eye motion.

FIG. 12 relates to an approach to analyzing eye movement. An example method 1200 relates to a context of using a home-based computer system to provide a proper interface and user experience to analyze eye movement, such as versions and ductions. Versions relate to both eyes moving, such as when a person looks to the left or to the right. Duction relates to unilateral movement of one eye. By having a patient use the online testing procedure because they are complaining of double vision, the system can record the user's eye movements to assess for any abnormalities in version or duction. For example, a user with a right sixth nerve palsy will be unable to move his right eye laterally or to the right, while his unaffected left eye will have full duction in all directions of gaze. A user with a right internuclear ophthalmoplegia will be unable to move the right eye to the left on left version but the right eye will be able to move to the left with accommodation, or when looking at a near object. Rapid eye movements called nystagmus that are associated with abnormal eye movements can be readily detected using this method.

In one example method to address or detect an issue with eye movement, a camera 406 of a device 402 can be used. A computer screen 118, a computer camera 108, a tablet or smart phone can be used. The camera 108 could be configured in the front or the back of a computing device 402. A method enables the user to position their face and eyes at the appropriate position from the device 402 that will allow the system to capture movement of eyes throughout in all positions of movement. The system can receive images or video of the eye and to allow for the analysis of eye movements to detect abnormal or pathologic changes related to clinical conditions such as strabismus, strokes, tumors, drugs, or other causes that can affect eye movements.

The method involves presenting a standard outline of the face whereby user positions his/her face to match the outline on the screen (1202). The system can provide input such as an audio instruction to have the user position their face as shown in the display. As an alternative, proper positioning can also be performed through an artificial intelligence-assisted facial recognition program with automated audio or visual directions to prompt the user to move their face into the proper position. Once proper positioning is attained, the method includes instructing the user to move their head in different directions while fixating on a visual object 120 on the screen (1204). In this context, the computer system can be fixed such as on a desktop computer with a camera facing the user. In another aspect, user can have a mobile electronic device in selfie mode and move the electronic device while fixating on a visual object on the screen, a wall, or a separate screen from the mobile device as their head is kept still. The instruction can tell the user to rotate their head up, down, right and left, while maintaining visual fixation on the object. The method then include receiving data regarding the user's eyes from the camera while the user moves their head in the instructed different directions (1206). Receiving the data can include recording a video of the user eye movement. The method also includes performing an analysis of the eye movement to determine clinical pathology and abnormal function (1208). The system can employ artificial intelligence algorithm which can be trained on known eye abnormalities in terms of the users looking in different directions. In another aspect, a doctor or clinician may manually review the received data, which can include a video of the user's different movement.

In another aspect, the system may automatically be programmed to control the camera 108 to focus or zoom in on the eyes of the user while they are moving in different directions. Have a more close-up view of the eyes can aid in analyzing the received data to determine if there are issues.

Figure 13:
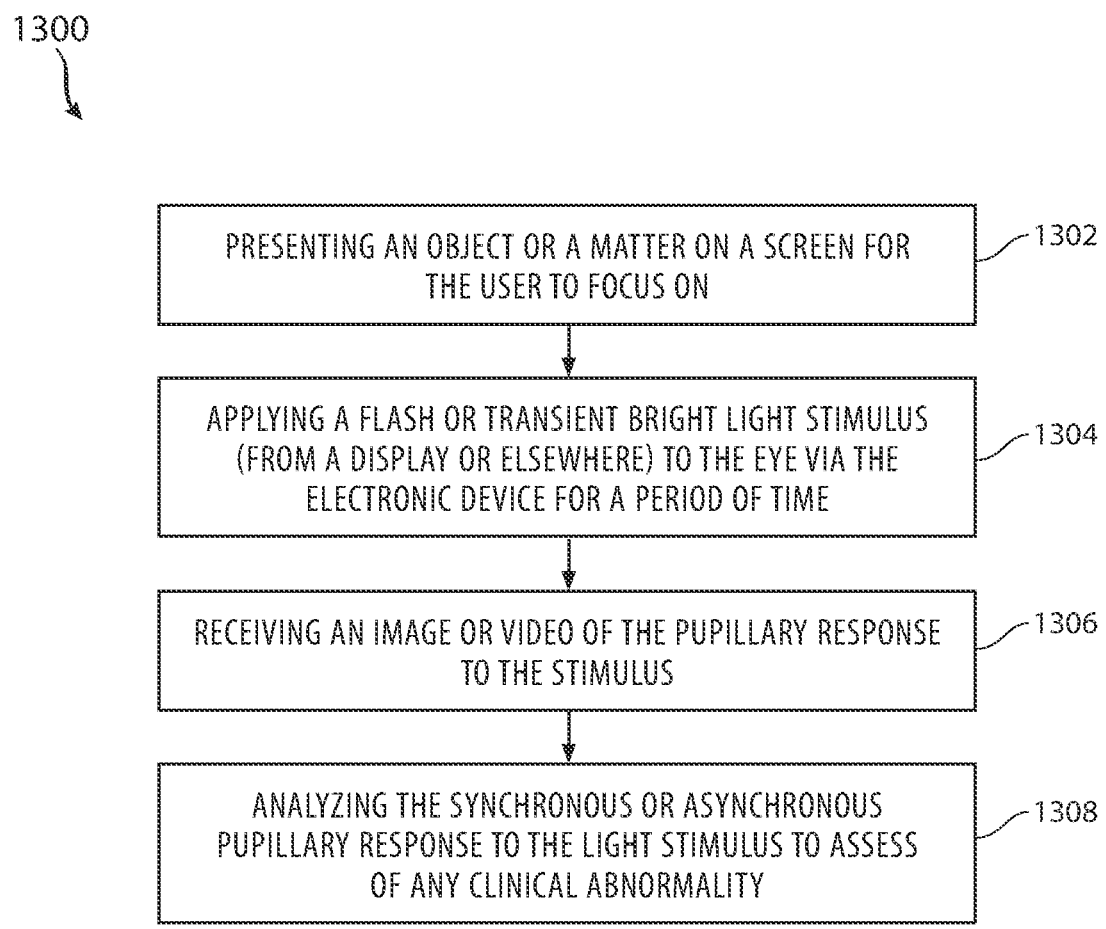
FIG. 13 illustrates an example method related to evaluating a pupillary response to stimulus.

FIG. 13 illustrates a method 1300 for analyzing pupillary responses via electronic or internet-connected devices. The system can analyze the way the pupil dilates and restricts to stimulus. For people with neurological problems, an issue arises because when a light is shined on the eye, it sees less light than it should and the pupil does not, for example, restrict as it should. Detecting the improper dilation or restriction can help to detect neurological problems. In some cases, a doctor will shine a light in one eye and evaluate the restriction in the pupil and then shine the light in a short period of time in the other eye to determine if the other eye restricts at the same rate, a different rate, and so forth and to determine whether there are neurological issues.

Photographic or video imaging of the eye call pupillometry can performed while the eye is looking at an object or pattern on the screen 118. The method can include presenting an object or a matter on a screen for the user to focus on (1302), and applying a flash or transient bright light stimulus (from a display, flashlight, flash, or elsewhere) to the eye via the electronic device for a period of time (1304). In the absence of a light flash device, the device LED screen can display high intensity background or light pattern. The pattern can direct light at one eye and then the other. The period of time, for example, can be 0.1 msec to 1 minute. Other times are contemplated as well. The method includes receiving an image or video of the pupillary response to the stimulus (1306) and analyzing the synchronous or asynchronous pupillary response to the light stimulus to assess of any clinical abnormality (1308). For increased accuracy and automation of analysis, an AI/machine learning algorithm may be used. Optical illusions to reduce accommodation that can constrict the pupils can be utilized to further enhance detection of pupillary response abnormalities. The received image or video can be streamed to a server (cloud or neural net) or analyzed locally on the user device. Furthermore, in one aspect, the test can be provided to a person who would hold the mobile device in place for the patient. In this case, the instructions would be provided for a separate person and be thus adjusted for that person to position the camera in the right place for the patient to have any respective test performed.

Dry is also a problem for users. This is mostly related to inflammation. The tear film is a thin layer of fluid, oil and other components over the eye. When there is inflammation the tear film becomes unstable and breaks up faster than it should. The image at the cornea becomes less clear. This next method seeks to determine the stability of the tear film.

Figure 14:
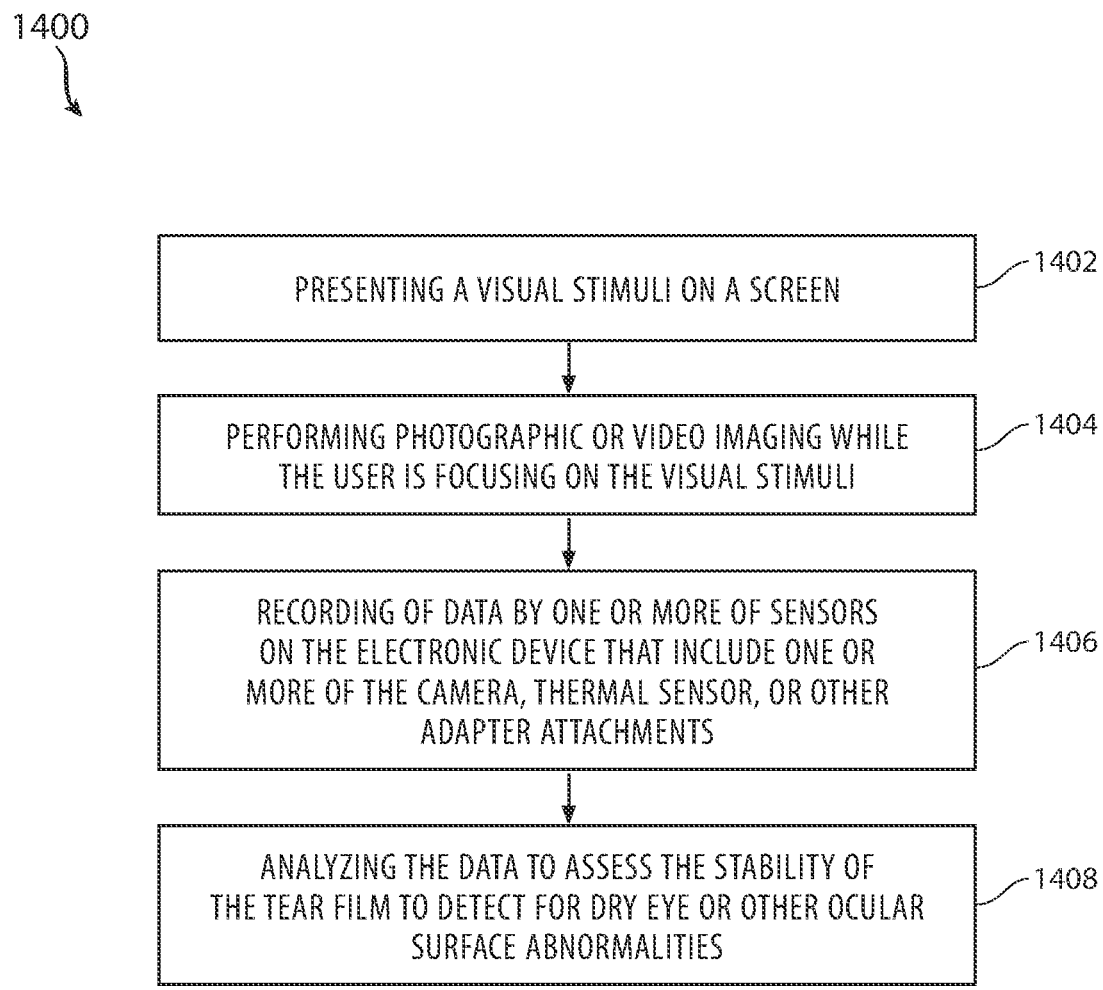
FIG. 14 illustrates an example method related to evaluating a status of a tear film of a user based on recording data from one or more sensors.

FIG. 14 illustrates a method 1400 for determining the stability (or instability) of the tear film by analyzing fluctuations in the recorded images of the ocular surface including the tear lake, cornea, conjunctiva, sclera, and eyelid margin. This relates to the functions of videokeratoscopy test module 140. The method includes presenting a visual stimuli on a screen (1402), and performing photographic or video imaging (e.g. videokeratography) while the user is focusing on the visual stimuli (1404). The visual stimuli can be patterns, objects, programs, or other stimuli. The method includes recording of data by one or more of sensors on the electronic device that include one or more of the camera, thermal sensor, or other adapter attachments (1406). For example, a thermal sensor can detect characteristics of the eyelids. The data can be visual data, thermal data or a combination of different types of data. The method includes analyzing (including machine learning/AI algorithm where appropriate) the data to assess the stability of the tear film to detect for dry eye or other ocular surface abnormalities (1408).

Next, a patient may need the curvature of their eye to be evaluated. The sclera curvature—OCT (optical coherence tomography) is used to analyze the curvature of the eye. Using expensive medical equipment, light from tiny pinholes are presented on the eye, if the light bounces back to a pinhole, it is spherical. If it does not bounce back and is diffused, the eye is not spherical. At a home of a patient, however, the specialized equipment cannot be used. The system in this case (client device 106, cloud environment 102) can present different wavelengths of color that can be shined on the eye. Depending how much scattering occurs on the different color wavelengths, the cloud environment 102 can determine the refractive status. The flash on a mobile device can be controlled by an application or the system to flash different colors rather than just a normal flash. The flash could be controlled further such that it does not operate in a red-eye reduction mode but adjusts its behavior to check for the refractive status of the eye. A screen of a computing device can also be used to present different colors on the eye. An application or controls provided through a browser from the cloud environment 102 can cause the system to control the flash or the display to present the proper color of light in the proper direction to be shined on the eye.

In another aspect, the facial recognition capabilities of a mobile device 106 can be implemented to detect the spherical nature of the eye. Again, adjustments might be made to the capabilities to improve the accuracy or focus of the capabilities on the eye region as improved detail might be needed only in the eye region and not elsewhere on the face. In this regard, the mobile device 106 could scan the eye with infrared light, use a beam of hundreds or thousands of dots that are invisible to the human eye, and create a depth map of the eye which can then be used to create a mathematical representation of the shape of the eye. The representation can then be evaluated to determine whether there is an issue with the curvature of the patient's eye. In one aspect, the facial recognition capabilities might be altered to transmit more beams of infrared light onto the particular eye region relative to other regions of the face in order to obtain greater data for determining eye curvature.

Figure 15:
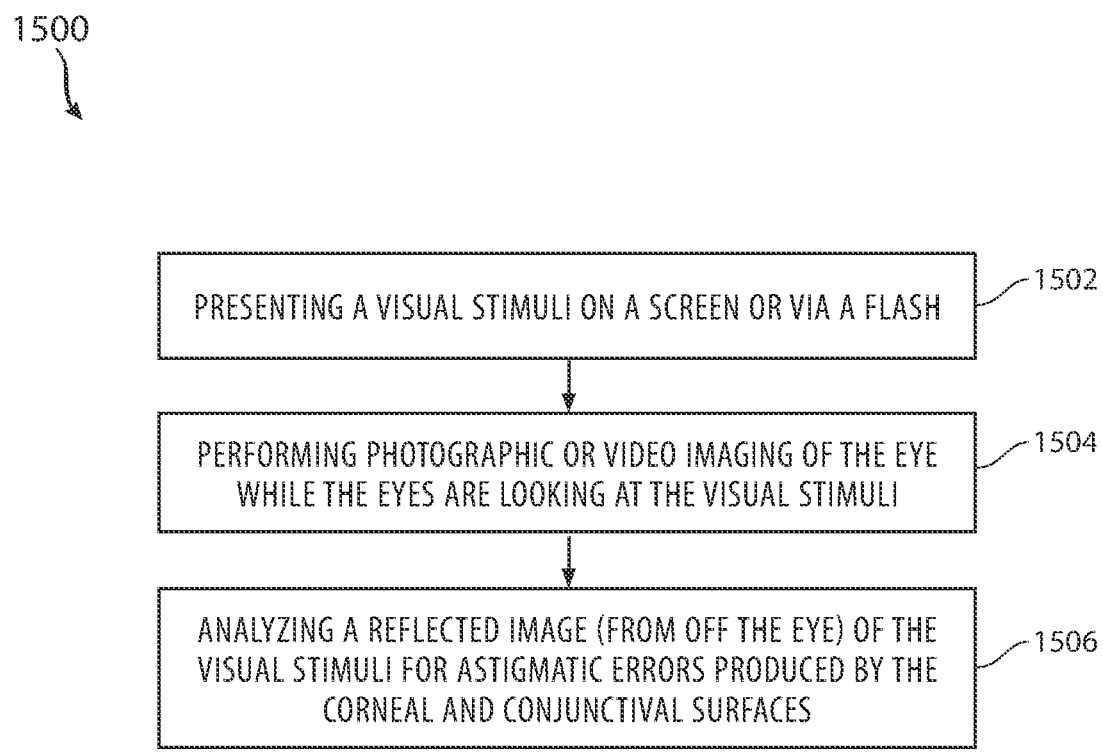
FIG. 15 illustrates an example method related to analyzing a reflected image from an eye to detect astigmatic errors.

FIG. 15 illustrates a method 1500 for assessing the refractive status of via electronic or internet-connected devices. The method includes presenting a visual stimuli on a screen or via a flash (1502) and performing photographic or video imaging of the eye while the eyes are looking at the visual stimuli (1504). The method includes analyzing a reflected image (from off the eye) of the visual stimuli for astigmatic errors produced by the corneal and conjunctival surfaces (1506). Using this data, the system can to allow for a calculation of axis of astigmatism that is critical for glasses, contact lens, or scleral lens fitting.

Alternatively, a wavefront-based analysis can be used to assess the refractive status of the eye by imaging the reflected pattern or light stimuli emanating from the electronic device using one or more cameras with different aperture sizes on the electronic device. This data can also be correlated to facial recognition data that maps the shape of the eye as well using mathematical representations generated from using infrared light to map the eye shape. As noted above, facial-recognition capabilities can also be extended to map the shape of the eye through imaging techniques.

Figure 16:
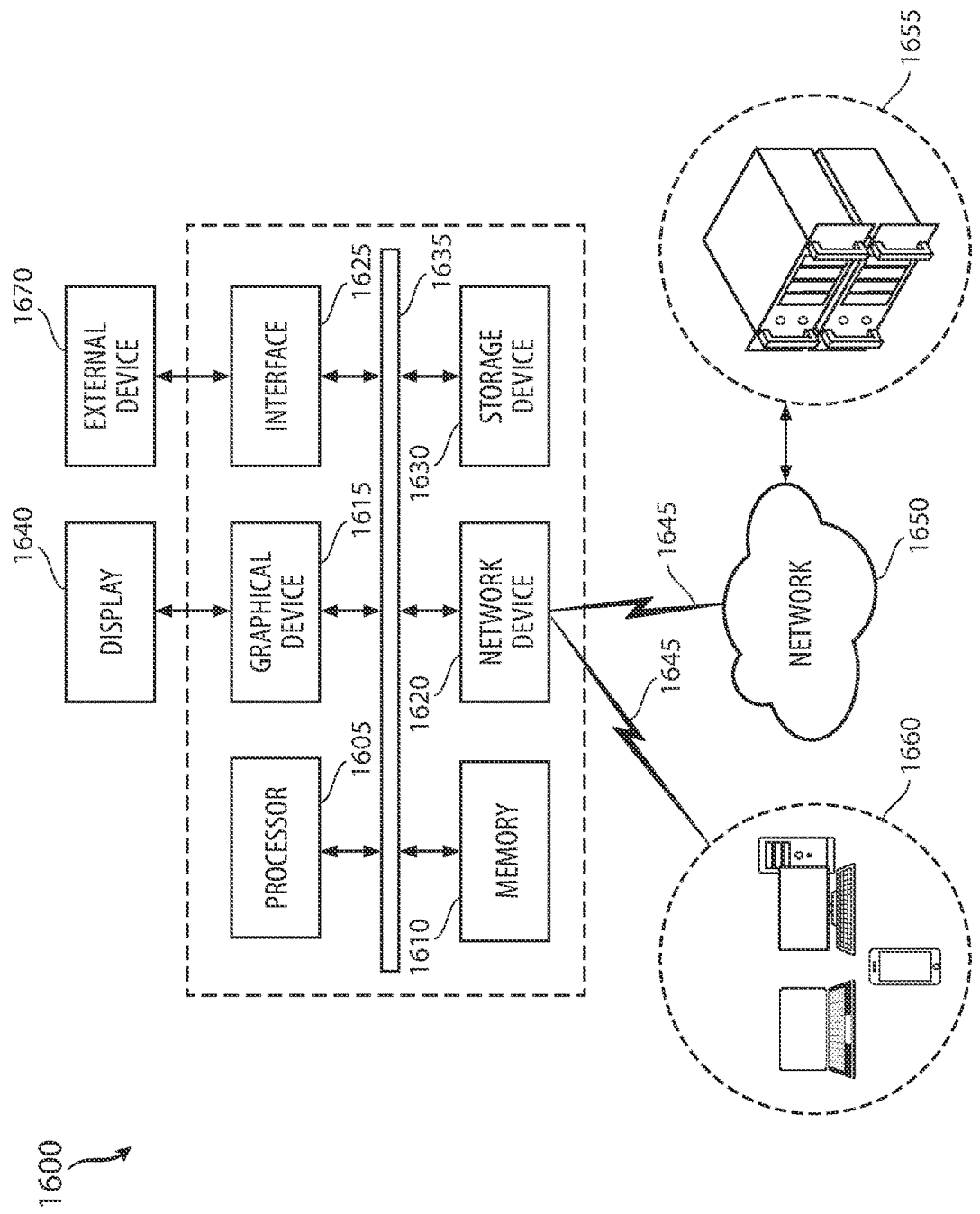
FIG. 16 illustrates an example system or device according to some aspects of this disclosure.

FIG. 16 illustrates an example computer system 1600 for implementing a part of the instant disclosure. For example, the example computer system 1600 may execute a client application for performing the instant disclosure. The example computer system 1600 includes a processor 1605, a memory 1610, a graphical device 1615, a network device 1620, interface 1625, and a storage device 1630 that are connected to operate via a bus 1635. The processor 1605 reads causes machine instructions (e.g., reduced instruction set (RISC), complex instruction set (CISC), etc.) that are loaded into the memory 1610 via a bootstrapping process and executes an operating system (OS) for executing application within frameworks provided by the OS. For example, the processor 1605 may execute an application that executes an application provided by a graphical framework such as Winforms, Windows Presentation Foundation (WPF), Windows User Interface (WinUI), or a cross platform user interface such as Xamarin or QT. In other examples, the processor 1605 may execute an application that is written for a sandbox environment such as a web browser.

A module can be programmed instructions stored in memory to control a processor to perform specific operations. So programmed, the computer becomes a special purpose computer specifically programmed to perform functions.

The processor 1605 controls the memory 1610 to store instructions, user data, operating system content, and other content that cannot be stored within the processor 1605 internally (e.g., within the various caches). The processor 1605 may also control a graphical device 1615 (e.g., a graphical processor) that outputs graphical content to a display 1640. In one example, the graphical device 1615 may be integral within the processor 1605. In yet another example, the display 1640 may be integral with the computer system 1600 (e.g., a laptop, a tablet, a phone, etc.).

The graphical device 1615 may be optimized to perform floating point operations such as graphical computations, and may be configured to execute other operations in place of the processor 1605. For example, the processor 1605 can be controlled by instructions to perform mathematical operations optimized for floating point math. For example, the processor 1605 may allocate instructions to the graphical device 1615 for operations that are optimized for the graphical device 1615. For instance, the graphical device 1615 may execute operations related to artificial intelligence (AI), natural language processing (NLP), vector math. The results may be returned to the processor 1605. In another example, the application executing in the processor 1605 may provide instructions to cause the processor 1605 to request the graphical device 1615 to perform the operations. In other examples, the graphical device 1615 may return the processing results to another computer system (i.e, distributed computing).

The processor 1605 may also control a network device 1620 that transmits and receives data using a plurality of wireless channels 1645 and at least one communication standard (e.g., Wi-Fi (i.e., 802.11ax, 802.11e, etc.), Bluetooth®, various standards provided by the 3rd Generation Partnership Project (e.g., 3G, 4G, 5G), or a satellite communication network (e.g., Starlink). The network device 1620 may wirelessly connect to a network 1650 to connect to servers 1655 or other service providers, such as a cloud environment provider or neural net. The network device 1620 may also be connected to the network 1650 via a physical (i.e., circuit) connection. The network device 1620 may also directly connect to local electronic device 1660 using a point-to-point (P2P) or a short range radio connection.

The processor 1605 may also control an interface 1625 that connects with an external device 1670 for bidirectional or unidirectional communication. The interface 1625 is any suitable interface that forms a circuit connection and can be implemented by any suitable interface (e.g., universal serial bus (USB), Thunderbolt, and so forth). The external device 1665 is able to receive data from the interface 1625 to process the data or perform functions for different applications executing in the processor 1605. For example, the external device 1665 may be another display device, a musical instrument, a computer interface device (e.g., a keyboard, a mouse, etc.), an audio device (e.g., an analog-to-digital converter (ADC), a digital-to-analog converter (DAC)), a storage device for storing content, an authentication device, an external network interface (e.g., a 5G hotspot), a printer, and so forth.

The principles or concepts disclosed herein can be performed by the client device 106, the cloud environment 102, another computing device such as a device with various input/output components at the office of a doctor or technician. Downloaded applications on user devices, "App Clip" code from Apple which includes small snippets of functional code, or browser-based user interfaces can be used in connection with the functionality disclosed herein.

It is noted that in one aspect, the steps disclosed herein can be practiced by a "system." The system can include the server, a cloud environment 102, a neural network, and/or one or more clients together, or might just be functionality performed by the server. The system could also be a client or a group of clients, such as clients in a particular geographic area or clients groups in some manner that are performing the client-based functions disclosed herein. Claims can be included which outline the steps that occur from the standpoint of any device disclosed herein. For example, the steps of transmission, calculation, and receiving of data can be claimed from the standpoint of a server device, a cloud environment, a neural network, a client device, or group of client devices depending on which embodiment is being covered. All such communication from the standpoint of an individual component or device can be included as within the scope of a particular embodiment focusing on that device.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. In another example, the use both of 3D depth sensors and/or the presentation of apparent 3D objects on a screen viewable by the user can be used both for aiding the user in position their head, as well as improvements in imaging of eye components depending on which test is being applied. Rather, the described features and steps are disclosed as examples of components of systems and methods within the scope of the appended claims.

Claim language reciting "at least one of" a set indicates that one member of the set or multiple members of the set satisfy the claim. For example, claim language reciting "at least one of A and B" means A, B, or A and B.

What is claimed is:

1. A method comprising:
   transmitting, from a cloud environment over the Internet and to a client device outside of a formal medical office, a graphical perimetry test that interrogates 0-100 degrees of a patient visual field of a patient, wherein the graphical perimetry test comprises an animated element which enhances patient concentration and maintains gaze direction of the patient, wherein the animated element is presented on the client device in a continuously dynamic manner for at least a part of the graphical perimetry test;
   transmitting, from the cloud environment to the client device, respective graphical stimuli at various periphery locations as part of the graphical perimetry test;

receiving, from the client device, respective patient input in response to the respective graphical stimuli; and generating, at the cloud environment and based on the respective patient input, a contrast-sensitivity map of a visual function for the patient.

2. The method of claim 1, wherein the animated element comprises a gamification approach to presenting the animated element.

3. The method of claim 1, wherein the animated element is positioned at a set position for a period of time during the graphical perimetry test.

4. The method of claim 1, wherein the graphical perimetry test represents an emulation of an office-based perimetry test.

5. The method of claim 1, further comprising:

applying a positioning algorithm which coordinates with a camera on the client device which is used to confirm that the patient has positioned their head to fit within a framed outline that is graphically presented on the client device as part of the graphical perimetry test.

6. The method of claim 5, wherein the positioning algorithm aids the patient in positioning a patient head a certain distance from a display on the client device.

7. The method of claim 6, further comprising:

receiving positional data at the cloud environment from the client device based on data viewed by the camera; and based on the positional data, transmitting instructions to the patient regarding moving the patient head to a proper position for taking the graphical perimetry test.

8. The method of claim 1, further comprising:

presenting an embedded virtual technician which the patient can access during the graphical perimetry test.

9. The method of claim 1, wherein the graphical perimetry test combines and integrates online visual acuity testing, color vision testing and central macular function testing along with testing perimetry for the patient.

10. A system comprising:

a processor; and a computer-readable storage device storing instructions which, when executed by the processor, cause the processor to perform operations comprising:

transmitting, over the Internet and to a client device outside of a formal medical office, a graphical perimetry test that interrogates 0-100 degrees of a patient visual field of a patient, wherein the graphical perimetry test comprises an animated element which enhances patient concentration and maintains gaze direction of the patient, wherein the animated element is presented on the client device in a continuously dynamic manner for at least a part of the graphical perimetry test;

transmitting, to the client device, respective graphical stimuli at various periphery locations as part of the graphical perimetry test;

receiving, from the client device, respective patient input in response to the respective graphical stimuli; and generating, based on the respective patient input, a contrast-sensitivity map of a visual function for the patient.

11. The system of claim 10, wherein the animated element comprises a gamification approach to presenting the animated element.

12. The system of claim 10, wherein the animated element is positioned at a set position for a period of time during the graphical perimetry test.

13. The system of claim 10, wherein the graphical perimetry test represents an emulation of an office-based perimetry test.

14. The system of claim 10, wherein the computer-readable storage device stores additional instructions which, when executed by the processor, cause the processor to perform operations further comprising:

applying a positioning algorithm which coordinates with a camera on the client device which is used to confirm that the patient has positioned their head to fit within a framed outline that is graphically presented on the client device as part of the graphical perimetry test.

15. The system of claim 14, wherein the positioning algorithm aids the patient in positioning a patient head a certain distance from a display on the client device.

16. The system of claim 15, wherein the computer-readable storage device stores additional instructions which, when executed by the processor, cause the processor to perform operations further comprising:

receiving positional data from the client device based on data viewed by the camera; and based on the positional data, transmitting instructions to the patient regarding moving the patient head to a proper position for taking the graphical perimetry test.

17. The system of claim 10, wherein the computer-readable storage device stores additional instructions which, when executed by the processor, cause the processor to perform operations further comprising:

presenting an embedded virtual technician which the patient can access during the graphical perimetry test.

18. The system of claim 10, wherein the graphical perimetry test combines and integrates online visual acuity testing, color vision testing and central macular function testing along with testing perimetry for the patient.

* * * * *